United States Patent
Schrock et al.

(10) Patent No.: US 10,780,261 B2
(45) Date of Patent: Sep. 22, 2020

(54) PACING OUTPUT K-FACTOR IMPROVEMENTS

(71) Applicant: Medtronic, Inc., Minneapolis, MN (US)

(72) Inventors: Anthony W. Schrock, Ham Lake, MN (US); James W. Busacker, St. Anthony, MN (US); Kevin E. Baumgart, St. Croix Falls, WI (US); Michael L. Hudziak, Stillwater, MN (US); James D. Reinke, Maple Grove, MN (US); John D. Wahlstrand, Shoreview, MN (US)

(*) Notice: Subject to any disclaimer, the term of this patent is extended or adjusted under 35 U.S.C. 154(b) by 156 days.

(21) Appl. No.: 15/900,831

(22) Filed: Feb. 21, 2018

(65) Prior Publication Data
US 2018/0250505 A1 Sep. 6, 2018

Related U.S. Application Data

(60) Provisional application No. 62/466,962, filed on Mar. 3, 2017.

(51) Int. Cl.
| | | |
|---|---|---|
| A61N 1/362 | (2006.01) | |
| A61N 1/02 | (2006.01) | |
| A61N 1/39 | (2006.01) | |
| A61N 1/372 | (2006.01) | |
| A61N 1/378 | (2006.01) | |
| G11C 5/14 | (2006.01) | |
| A61N 1/37 | (2006.01) | |

(52) U.S. Cl.
CPC ............ *A61N 1/025* (2013.01); *A61N 1/362* (2013.01); *A61N 1/37211* (2013.01); *A61N 1/3956* (2013.01); *A61N 1/371* (2013.01); *A61N 1/3782* (2013.01); *A61N 1/3981* (2013.01); *G11C 5/145* (2013.01)

(58) Field of Classification Search
None
See application file for complete search history.

(56) References Cited

U.S. PATENT DOCUMENTS

| | | |
|---|---|---|
| 4,031,899 A | 6/1977 | Renirie |
| 4,345,604 A | 8/1982 | Renirie |
| 4,402,322 A | 9/1983 | Duggan |
| 5,387,228 A | 2/1995 | Shelton |
| 5,423,866 A * | 6/1995 | Ekwall .................. A61N 1/362 607/11 |

(Continued)

OTHER PUBLICATIONS (PCT/US2018/020641) PCT Notification of Transmittal of the International Search Report and the Written Opinion of the International Searching Authority, dated May 22, 2018, 14 pages.

*Primary Examiner* — Kennedy Schaetzle
(74) *Attorney, Agent, or Firm* — Medtronic, Inc.

(57) ABSTRACT

In an example, an implantable medical device (IMD) includes a hold capacitor configured to deliver an electrical therapy pulse, and charge pump circuitry configured to transfer energy from the battery to the hold capacitor. In this example, the charge pump circuitry comprises a plurality of capacitors, and switching circuitry configured to put the charge pump circuitry into a K-factor mode selected from a group of K-factor modes by opening and closing a combination of switches connected to the plurality of capacitors.

18 Claims, 28 Drawing Sheets

(56) References Cited

U.S. PATENT DOCUMENTS

| | | | |
|---|---|---|---|
| 5,697,956 A * | 12/1997 | Bornzin | A61N 1/3712 |
| | | | 607/28 |
| 5,836,981 A | 11/1998 | Chang et al. | |
| 5,876,423 A | 3/1999 | Braun | |
| 5,948,004 A | 9/1999 | Weijand et al. | |
| 5,964,787 A | 10/1999 | Kerver et al. | |
| 6,289,246 B1 | 9/2001 | Money | |
| 6,353,760 B1 | 3/2002 | Lyden | |
| 6,363,283 B1 | 3/2002 | Lyden | |
| 6,892,096 B2 | 5/2005 | Lyden | |
| 7,605,640 B2 | 10/2009 | Ki et al. | |
| 7,715,911 B2 | 5/2010 | Vernon et al. | |
| 7,872,884 B2 | 1/2011 | Parramon et al. | |
| 7,923,865 B2 * | 4/2011 | Melse | G11C 5/145 |
| | | | 307/82 |
| 8,290,583 B2 | 10/2012 | Vernon et al. | |
| 9,002,447 B2 | 4/2015 | Gordon et al. | |
| 2002/0068957 A1 * | 6/2002 | Wolfe | A61N 1/025 |
| | | | 607/2 |
| 2003/0167407 A1 | 9/2003 | Howard | |
| 2004/0167407 A1 | 8/2004 | Roberts | |
| 2009/0326624 A1 | 12/2009 | Melse | |
| 2010/0069992 A1 * | 3/2010 | Aghassian | A61N 1/37229 |
| | | | 607/32 |
| 2012/0197330 A1 | 8/2012 | Crutchfield et al. | |
| 2014/0277283 A1 | 9/2014 | Reinke et al. | |
| 2015/0251010 A1 | 9/2015 | Gordon et al. | |

* cited by examiner

FIG. 6

| | Sw1 | Sw2 | Sw3 | Sw4 | Sw5 | Sw6 | Sw7 | Sw8 | Sw9 | Sw10 | Sw11 | Sw12 | Sw13 | Sw14 | Sw15 | Sw16 | Sw17 | Sw18 | Sw19 | Sw20 |
|---|---|---|---|---|---|---|---|---|---|---|---|---|---|---|---|---|---|---|---|---|
| Charge Mode A | X |   | X | X |   | X |   |   |   |   |   |   |   |   |   |   |   |   |   |   |
| Charge Mode A 3/4x | X | X | X | X | X | X |   |   |   |   |   |   |   |   |   |   |   |   |   |   |
| Charge Mode A 5/4x | X |   | X | X | X | X |   |   |   |   |   |   |   |   |   |   |   |   |   |   |
| 1/2x | X | X | X | X |   |   | X | X |   |   |   |   |   |   |   |   |   |   |   |   |
| 3/4x | X | X | X | X |   |   |   | X |   | X |   |   |   |   |   |   |   |   |   |   |
| 5/4x |   | X | X | X |   |   |   |   |   |   | X | X |   |   |   |   |   |   |   |   |
| 3/2x | X | X | X | X |   |   |   |   |   |   | X | X |   |   |   |   |   |   |   |   |
| 2x |   | X |   |   | X | X | X |   |   |   |   |   | X |   | X | X | X |   |   |   |
| 5/2x |   | X |   | X |   |   |   |   |   |   |   |   | X | X | X |   |   |   |   |   |
| 3x |   |   | X |   |   |   |   |   |   |   |   |   |   |   |   |   |   | X |   |   |
| Charge Mode B | X | X | X | X |   | X |   |   |   |   |   |   |   |   |   |   |   |   |   |   |
| 1/2x | X | X | X | X |   |   | X | X |   |   |   |   |   |   |   |   |   |   |   |   |
| 3/2x |   | X | X | X |   |   | X | X |   |   |   |   |   |   |   |   |   |   |   |   |
| 2x |   | X |   | X | X | X |   |   | X |   |   | X |   |   |   |   |   |   |   |   |
| 5/2x |   | X |   |   |   |   |   | X | X |   |   |   | X | X | X | X | X | X |   |   |
| 3x | X | X |   | X |   |   |   |   |   |   |   |   |   |   |   |   |   |   |   |   |
| 7/2x |   | X |   |   |   |   |   |   | X | X |   |   |   |   |   | X | X |   | X | X |
| 4x | X | X | X |   |   |   |   |   |   |   |   |   |   |   |   | X | X |   | X | X |

Pump Mode A / Pump Mode B — PCP Switches

FIG. 10

PACING OUTPUT K-FACTOR IMPROVEMENTS

CROSS-REFERENCE TO RELATED APPLICATIONS

This application claims the benefit of U.S. provisional application Ser. No. 62/466,962, filed Mar. 3, 2017, the entire content of which is incorporated by reference herein.

TECHNICAL FIELD

This disclosure relates to implantable medical devices, and more particularly, to implantable medical devices that deliver cardiac pacing.

BACKGROUND

A wide variety of implantable medical devices for delivering a therapy or monitoring a physiologic condition have been clinically implanted or proposed for clinical implantation in patients. In some cases, implantable medical devices (IMD) deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for sensing or delivery of stimulation. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation, via electrodes of one or more implantable leads. In some cases, such an implantable medical device may sense intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver defibrillation electrical signals to a patient's heart upon detecting ventricular fibrillation. Pacing signals typically have a lower energy than the cardioversion or defibrillation signals.

Patients with heart failure are, in some cases, treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle to synchronize its contraction with that of the other ventricular, such as pacing the left ventricle to synchronize its contraction with that of the right ventricle. CRT is one example of a variety of modes of cardiac pacing in which stimulation is delivered to one chamber or location at a time that is an interval before or after an event at another chamber or location. The event at the other chamber or location may be the delivery of a pacing pulse to the other chamber or location, or the detection of an intrinsic cardiac depolarization at the other chamber or location.

In some examples, a first pair of electrodes delivers a pacing pulse to a chamber, and the same or a different pair of electrodes detects an electrical signal, e.g., evoked response, in the chamber indicative of capture. In other examples, a device detects a mechanical contraction of the heart at the target site as evidence of capture of the heart by the pacing stimulus. In general, capture threshold determination or management involves delivery of pacing stimuli at incrementally increasing or decreasing magnitudes, e.g., voltage or current amplitudes or pulse widths, and identification of the magnitude at which capture or loss of capture occurs.

BRIEF DESCRIPTION OF DRAWINGS

FIG. 6 is a table showing the k-factors for each of the charge and pump modes and the corresponding switch closures used to achieve those modes for the charge pump FIG. 5A.

FIG. 10 is a table showing a minimum supply voltage needed for the selected pacing amplitude (Vamp) and k-factor, for an example implementation of the techniques of this disclosure.

DETAILED DESCRIPTION

Figure 1:
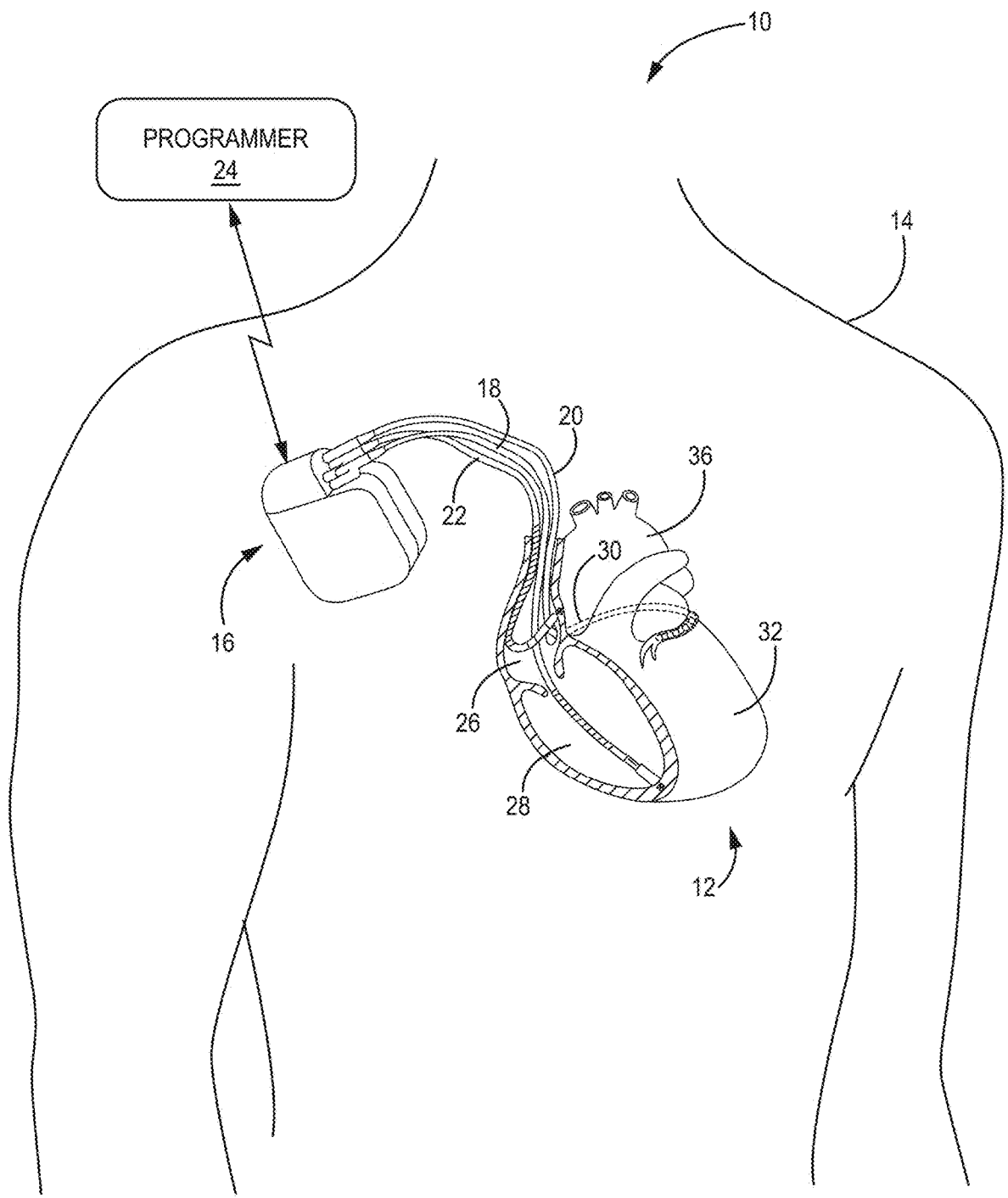
FIG. 1 is a conceptual diagram illustrating an example system that may be used to provide therapy to and/or monitor a heart of a patient.

Cardiac pacemakers provide therapeutic stimulation to the heart by delivering electrical therapy signals, such as electrical pulses for pacing. A charge pump in the cardiac pacemaker delivers pacing pulse energy from the battery to a hold capacitor, and the hold capacitor delivers the therapy signals to the chambers of the heart. The voltages needed for the therapy signals to effectively pace the heart may vary from patient to patient and from chamber to chamber within a patient. Even within the same chamber for the same patient, the voltage needed to effectively pace the heart may vary over time. Additionally, the output voltage of the battery in the pacemaker typically varies over time.

The charge pump supplies to the hold capacitor a voltage that is equal to the battery voltage multiplied by a K factor. The relationship between battery voltage and charge pump voltage is shown by equation 1 below, and the relationship between battery current and charge pump current is shown by equation 2 below.

$$V_{Charge\ Pump} = V_{Battery} \times K_{factor} \quad (1)$$

$$I_{Battery} = I_{Charge\ Pump} \times K_{factor} \quad (2)$$

The K factor may be less than, equal to, or greater than one. For example, without any system losses, a 3V battery with a K-factor of ⅓ produces a 1V pacing voltage. As another example, without any system losses, a 3V battery with a K-factor of 3/2 produces a 4.5V pacing voltage. The charge pump typically outputs a voltage higher than the target pacing voltage. Thus, higher pacing voltages require higher K factors, and lower pacing voltages require lower K factors.

For a typical pacemaker, current from the battery for pacing is the most significant load on the battery, particularly for CRT, heart failure patients that are paced a greater percentage of the time and at relatively greater voltages. The most efficient K factor, i.e., the K factor that minimizes battery draw and maximizes battery life, is the K factor that provides the required pacing output voltage for the least current. For example, without any system losses, a 1V pacing voltage can be generated from a 3V battery with a K-factor of ⅓, which results in the current draw from the battery being reduced to ⅓, compared to directly charging the hold capacitor from the battery.

To account for the pacing voltage variations and battery voltage variations described above, charge pumps are typically designed to operate in a plurality of discrete modes, with each mode corresponding to a different K factor. In existing techniques, the number of modes (i.e., the number of K-factor ratios) is typically limited largely due to the added capacitor components and IC switches required to implement the ratios in the charge pump circuitry. An advantage of having increased modes is the ability to use K factors that more closely match the output pacing voltage to the available battery voltage, which potentially reduces current draw on the battery and thus increases battery life.

Typically, charge pumps are configured to implement K factors that range from ½ to 4 in increments of ½. The charge pump architecture of this disclosure is designed to achieve a larger number of k-factor multipliers compared to previous architectures while minimizing the number of external components required. More specifically, this disclosure describes techniques for adding K-factors of 0.75× and 1.25×. The techniques of this disclosure utilize a 2-phase clock to provide the added ratios with minimal additional capacitors or added clock phases. Approximately 2.0V is a common pacing voltage. A new battery may have an output voltage of slightly over 3.0V, with the output voltage remaining over 2.8V for a majority of the battery's lifetime, making 0.75× a preferred K factor for a number of common pacing scenarios. As the battery ages, the output voltage may drop sufficiently that a K factor of 1.25× is needed for the remainder of the battery capacity. The added 0.75× and 1.25× K-factors may thus enable a considerable battery current drain savings and longevity increase when compared to existing charge pumps that only offer 1.0×, 1.5×, and 2.0× K-factors.

This disclosure also describes techniques for implementing automatic switching of K-factors based on charged hold capacitor voltage. Battery current is minimized by selecting the smallest k-factor multiplier that will still achieve the targeted pacing voltage, so more k-factors allows for better current drain optimization.

FIG. 1 is a conceptual diagram illustrating an example system 10 that may be used to monitor and/or provide therapy to heart 12 of patient 14. Patient 14 ordinarily, but not necessarily, will be a human. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. The techniques of this disclosure are not limited to an IMD with a specific number of leads and may be implemented in devices that use more or fewer leads. For example, the techniques of this disclosure may also be implemented in single chamber or dual chamber devices that use fewer leads than IMD 16. The techniques of this disclosure may also be implemented in extravascular devices that use no leads in the heart and only a subcutaneous or under sternum lead. The techniques of this disclosure may also be implemented in intracardiac devices, such as a transcatheter pacemaker, that have no leads extending from the device.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12, e.g., for bradycardia pacing, CRT, or anti-tachycardia pacing (ATP), based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
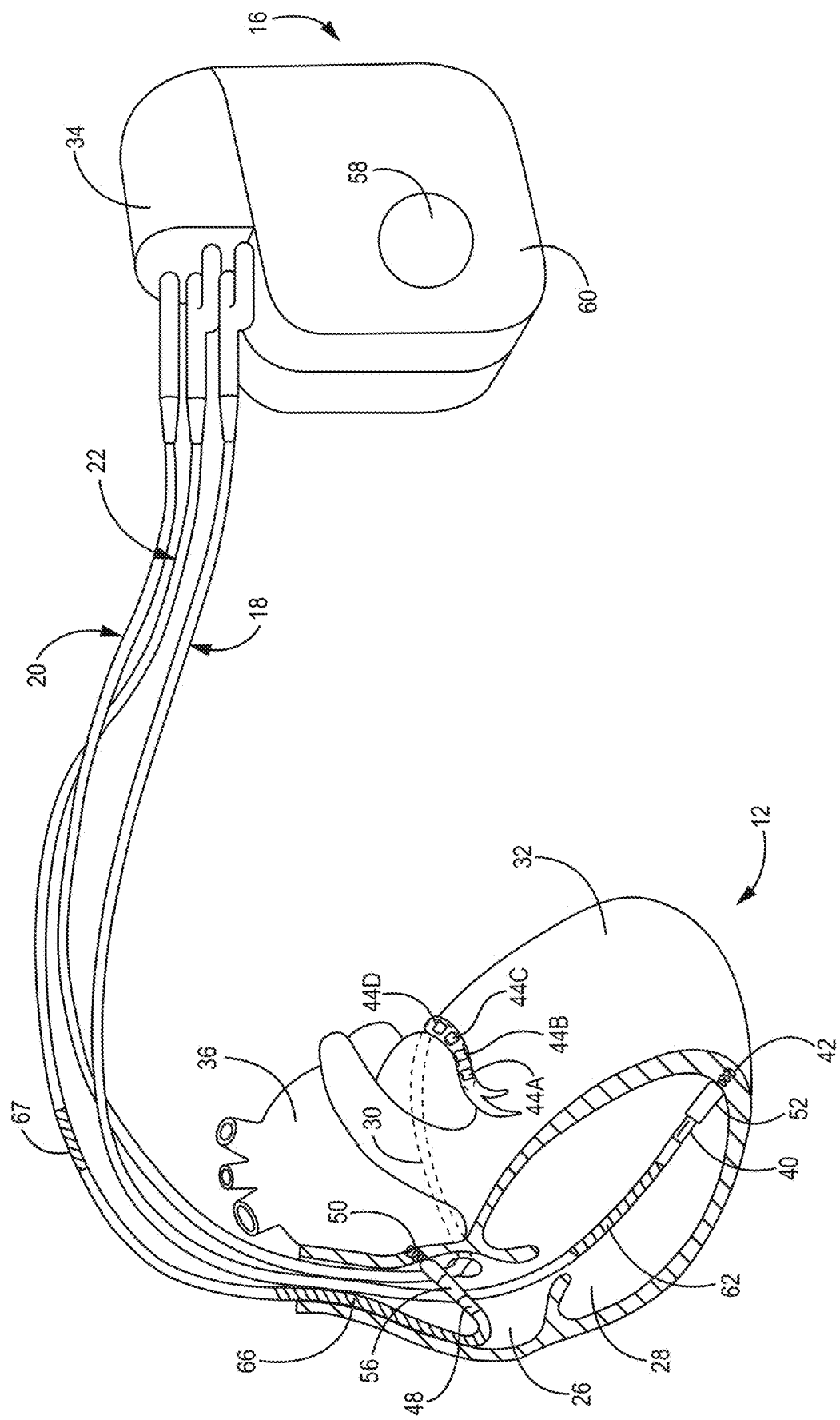
FIG. 2 is a conceptual diagram illustrating the example implantable medical device (IMD) and the leads of the system shown in FIG. 1 in greater detail.

FIG. 2 is a conceptual diagram illustrating IMD 16 and leads 18, 20, and 22 of therapy system 10 in greater detail. Leads 18, 20, 22 may be electrically coupled to a signal generator and a sensing circuitry of IMD 16 via connector block 34.

Each of the leads 18, 20, 22 includes an elongated insulative lead body carrying one or more conductors. Electrodes 40 and 42 are located adjacent to a distal end of lead 18 and electrodes 48 and 50 are located adjacent to a distal end of lead 22. In some example configurations, lead 20 may be a quadripolar lead and, as such, include four electrodes, namely electrodes 44A-44D, which are located adjacent to a distal end of lead 20. Electrodes 40, 44A-44D, and 48 may take the form of ring electrodes, and electrodes 42 and 50 may take the form of extendable helix tip electrodes mounted retractably within insulative electrode heads 52 and 56, respectively.

Leads 18 and 22 also include elongated intracardiac electrodes 62 and 66 respectively, which may take the form of a coil. In addition, one of leads 18, 20, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44A-44D, 48, 50, 62, 66 and 67 may be electrically coupled to a respective one of the conductors within the lead body of its associated lead 18, 20, 22, and thereby individually coupled to the signal generator and sensing circuitry of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44A-44D, 48, 50, 58, 62, 66 and 67. The electrical signals are conducted to IMD 16 via the respective leads 18, 20, 22, or in the case of housing electrode 58, a conductor coupled to the housing electrode. MID 16 may sense such electrical signals via any combination of electrodes 40, 42, 44A-44D, 48, 50, 58, 62, 66 and 67. Furthermore, any of the electrodes 40, 42, 44A-44D, 48, 50, 58, 62, 66 and 67 may be used for unipolar sensing in combination with housing electrode 58.

In some examples, IMD 16 delivers pacing pulses via combinations of electrodes 40, 42, 44A-44D, 48 and 50 to produce depolarization of cardiac tissue of heart 12. In some examples, IMD 16 delivers pacing pulses via any of electrodes 40, 42, 44A-44D, 48 and 50 in combination with housing electrode 58 in a unipolar configuration. For example, electrodes 40, 42, and/or 58 may be used to deliver RV pacing to heart 12. Additionally or alternatively, electrodes 44A-44D and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 66 and 67, and housing electrode 58. Electrodes 58, 62, and 66 may also be used to deliver cardioversion pulses to heart 12. Electrodes 62, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. Further, in some examples, a therapy system includes a leadless, e.g., transcatheter and/or intracaradiac, pacemaker that is configured to deliver pacing pulses to the heart without leads, e.g., via electrodes formed on or as part of its housing. Such leadless pacemakers may be configured to implement the pacing circuitry and techniques described herein.

Figure 3:
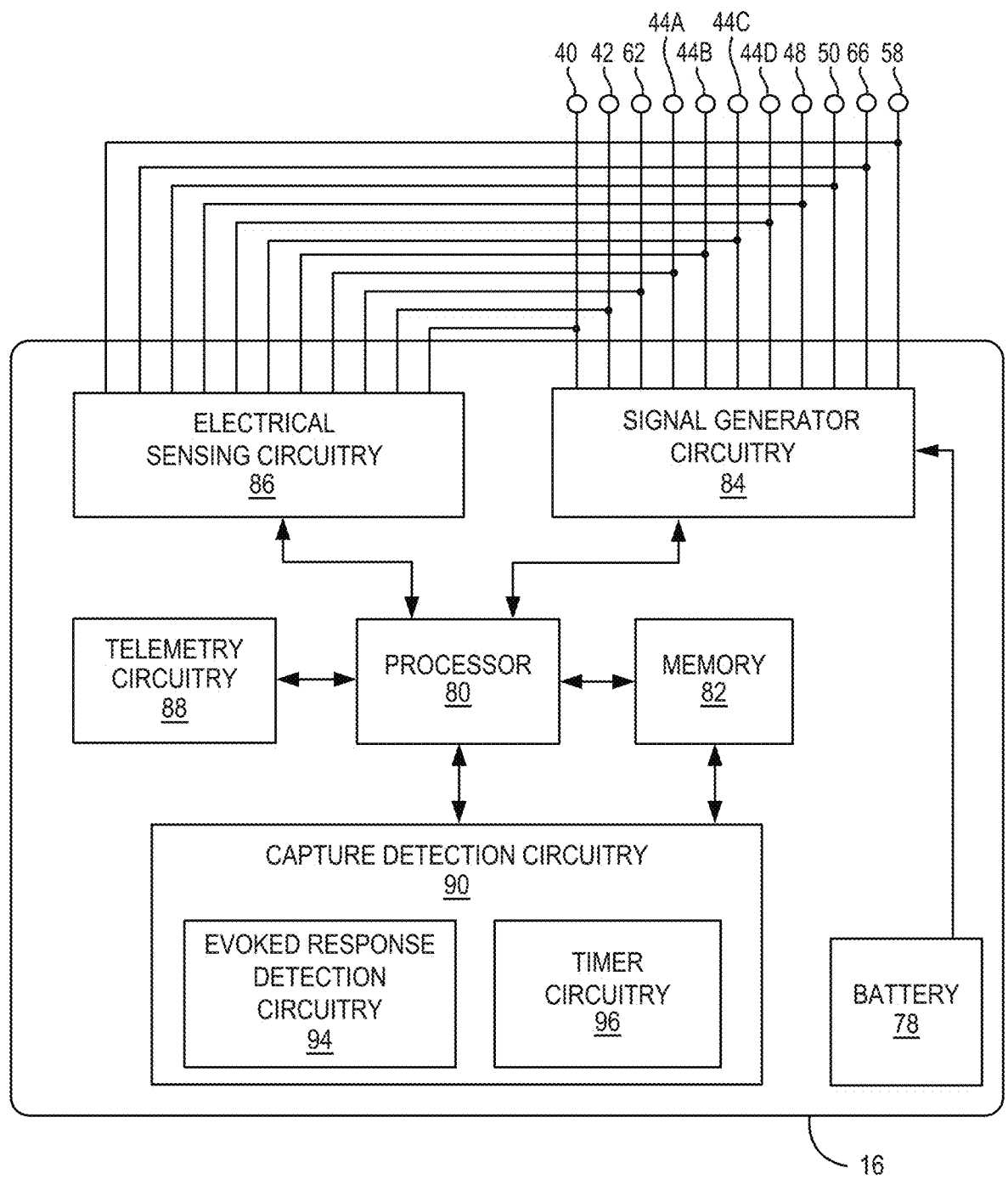
FIG. 3 is a block diagram illustrating an example configuration of an implantable medical device.

FIG. 3 is a block diagram illustrating one example configuration of IMD 16. The techniques of this disclosure are not limited to a specific type of IMD and may be implemented into a wide variety of IMDs, including IMDs that include features not described with respect to IMD 16 and IMDs that do not include certain features of IMD 16. For example, although Imp 16 is an intravascular IMD, the techniques of this disclosure may also be implemented in an extravascular IMD.

In the example illustrated by FIG. 3, IMD 16 includes a battery 78, a processor 80, memory 82, signal generator 84, electrical sensing circuitry 86, and telemetry circuitry 88.

IMD 16 further includes capture detection circuitry 90, which itself includes evoked response detection circuitry 94 and timer circuitry 96. Memory 82 may include computer-readable instructions that, when executed by processor 80, cause IMD 16 and processor 80 to perform various functions attributed throughout this disclosure to IMD 16, processor 80, or capture detection circuitry 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Battery 78 supplies energy to IMD 16, including the energy used for generating pacing signals. Although in FIG. 3 battery 78 is only shown as being connected signal generator 84, it should be understood that battery 78 may supply all the power for all functionality of IMD 16.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, capture detection circuitry 90, evoked response detection circuitry 94, and timer circuitry 96 may be stored or encoded as instructions in memory 82 that are executed by processor 80.

Processor 80 controls signal generator 84 to deliver stimulation therapy, e.g., cardiac pacing or CRT, to heart 12 according to a selected one or more therapy programs, which may be stored in memory 82. Signal generator 84 is electrically coupled to electrodes 40, 42, 44A-44D, 48, 50, 58, 62, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12 via selected combinations of electrodes 40, 42, 44A-44D, 48, 50, 58, 62, and 66. In some examples, signal generator 84 is configured to delivery cardiac pacing pulses. In other examples, signal generator 84 may deliver pacing or other types of stimulation in the form of other signals, such as sine waves, square waves, or other substantially continuous time signals.

Signal generation circuitry 84 may include, for example, voltage conversion circuitry, charge pump circuitry, and one or more capacitors, e.g., for the delivery of pacing pulses. Signal generator 84 may also include a switch circuitry (not shown) and processor 80 may use the switch circuitry to select, e.g., via a data/address bus, which of the available electrodes are used to deliver pacing pulses. Processor 80 may also control which of electrodes 40, 42, 44A-44D, 48, 50, 58, 62, and 66 is coupled to signal generator 84 for generating stimulus pulses, e.g., via the switch circuitry. The switch circuitry may include a switch array, switch matrix, multiplexer, or any other type of switching device suitable to selectively couple a signal to selected electrodes.

Electrical sensing circuitry 86 monitors signals from at least one of electrodes 40, 42, 44A-44D, 48, 50, 58, 62, or 66 in order to monitor electrical activity of heart 12. Electrical sensing circuitry 86 may include, for example, filters and amplifiers to condition an electrical signal sensed at the electrodes and/or detect particular features within the signal. Electrical sensing circuitry 86 may also include a switch circuitry to select which of the available electrodes are used to sense the cardiac activity. In some examples, processor 80 selects the electrodes that function as sense electrodes, or the sensing vector, via the switch circuitry within electrical sensing circuitry 86.

Electrical sensing circuitry 86 includes multiple detection channels, each of which may be selectively coupled to respective combinations of electrodes 40, 42, 44A-44D, 48, 50, 58, 62, or 66 to detect electrical activity of a particular chamber of heart 12. Each detection channel may comprise an amplifier that outputs an indication to processor 80 in response to detection of an event, such as a depolarization, in the respective chamber of heart 12. In this manner, processor 80 may detect the occurrence of R-waves and P-waves in the various chambers of heart 12.

Memory 82 stores intervals, counters, or other data used by processor 80 to control the delivery of pacing pulses by signal generator 84. Such data may include intervals and counters used by processor 80 to control the delivery pacing pulses to one or both of the left and right ventricles for CRT. The intervals and/or counters are, in some examples, used by processor 80 to control the timing of delivery of pacing pulses relative to an intrinsic or paced event, e.g., in another chamber.

In one example, capture detection circuitry 90 uses signals from electrical sensing circuitry 86 to detect capture and/or inadequate capture when signal generator 84 delivers a pacing pulse. Via the switching circuitry, processor 80 may control which of electrodes 40, 42, 44A-44D, 48, 50, 58, 62, and 66 is coupled to electrical sensing circuitry 86 to detect an evoked response subsequent to the delivery of a pacing pulse to a chamber, e.g., the LV, for the determination of whether the pacing pulse captured the chamber. Memory 82 may store predetermined intervals or voltage thresholds which define whether a detected signal has an adequate magnitude and is appropriately timed relative to the pacing pulse to be considered an evoked response. In some examples, a channel of electrical sensing circuitry 86 used to detect capture comprises an amplifier which provides an indication to processor 80 when a detected signal has an adequate magnitude.

Processor 80 controls the selection of electrode configurations for delivering pacing pulses and for detecting capture and/or loss of capture. Processor 80, for example, may communicate with signal generator 84 to select two or more stimulation electrodes in order to generate one or more pacing pulses for delivery to a selected chamber of heart 12. Processor 80 may also communicate with electrical sensing circuitry 86 to select two or more sensing electrodes for capture detection based on the chamber to which the pacing pulse is delivered by signal generator 84.

Capture detection circuitry 90, in the example of FIG. 3, is capable of detecting capture and LOC during capture detection tests. Capture detection circuitry 90 uses timer circuitry 96 to determine when to deliver pacing pulses. In addition, as seen in FIG. 3, capture detection circuitry 90 further includes evoked response detection circuitry 94 for detecting the amplitude and timing of an evoked response.

Using certain techniques of this disclosure, capture detection circuitry 90 may determine pacing capture thresholds for each of a plurality of pacing vectors by, for each of the vectors, delivering pacing pulses at various voltage levels, and determining a voltage at which capture/loss-of-capture (LOC) occurs.

Figure 4:
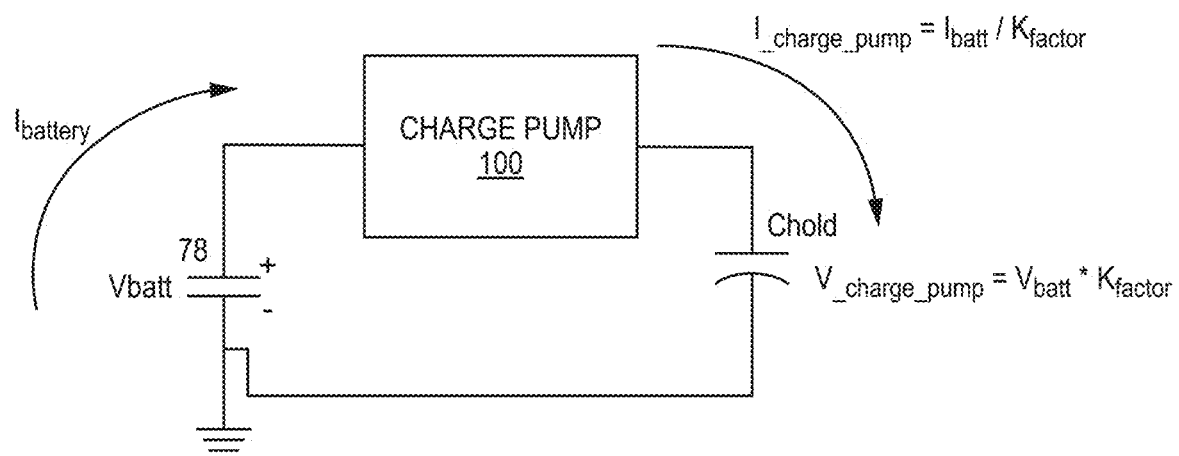
FIG. 4 is a block diagram showing an overview of a charge pump.

Signal generator 84 may include a charge pump in accordance with the techniques of this disclosure. FIG. 4 shows an example of a charge pump 100, which may be included in signal generator 84. Charge pump 100 is connected to battery 78 and produces an output voltage on Chold that is equal to the voltage of battery 78 multiplied by a K factor.

Figure 5A:
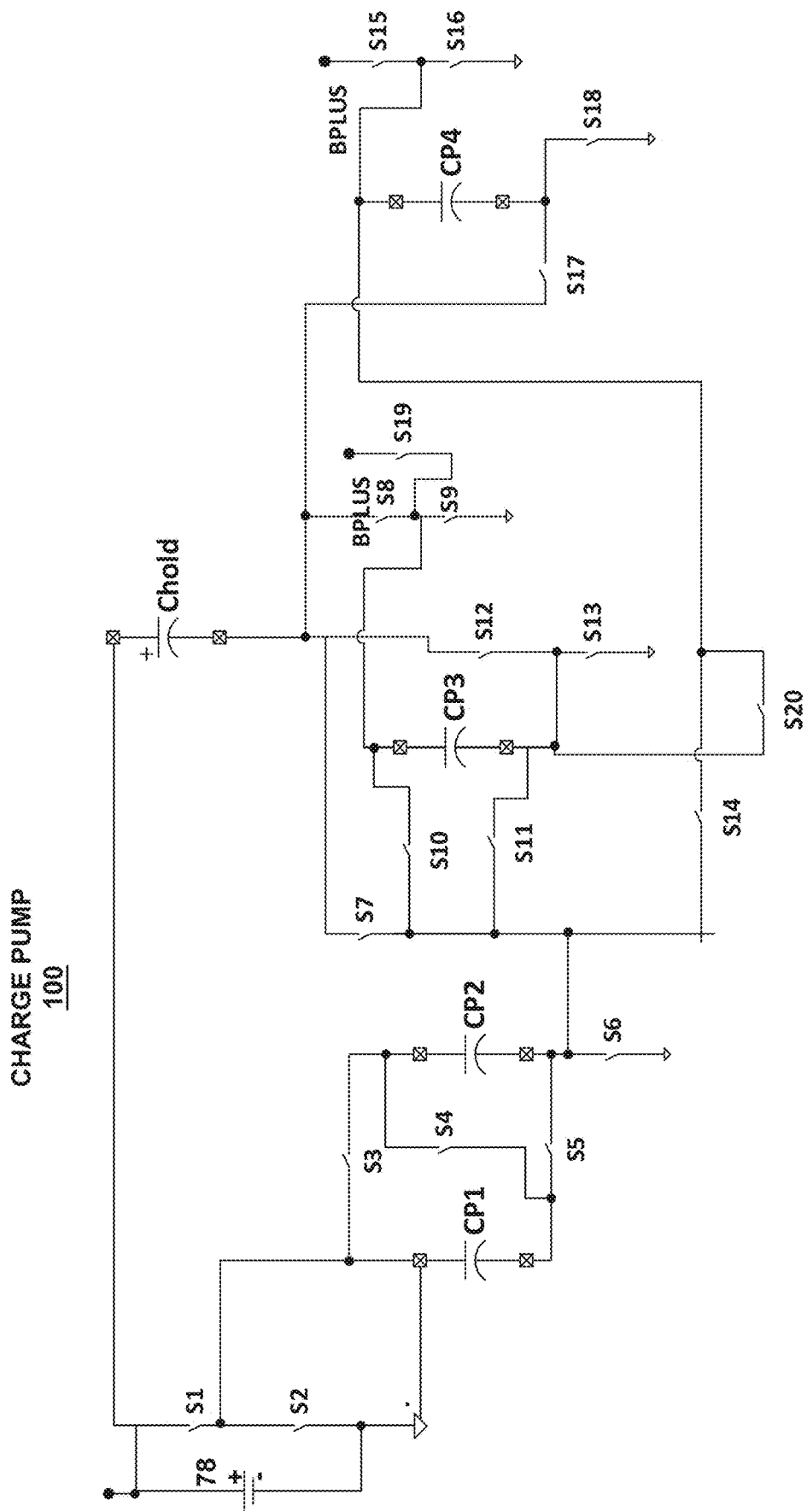
FIG. 5A is a schematic showing a more detailed implementation of the charge pump of FIG. 4.

FIG. 5A shows a more detailed implementation of charge pump 100 in accordance with the techniques of this disclosure. Charge pump 100 is connected to battery 78 and delivers an output voltage to hold capacitor 104 (Chold 104). Charge pump 100 includes capacitors, CP1, CP2, CP3, and CP4, as well as switches S1 through S20. It should be understood that, for ease of explanation, FIG. 5A represents a simplified version of an actual charge pump. For example, in a real-world implementation, Chold 104 may actually be implemented as four hold capacitors, with any switch (any of switches S1 to S20) being implemented as four switches between a common node and the corresponding hold capacitor. The four hold capacitors may correspond to the four chambers of the heart, Atrial (A), Right Ventricular (RV), Left Ventricular (LV) and Support (S). The Support (S) hold capacitor may be utilized at times in parallel with another hold capacitor to provide higher current capacity during rapid pacing demands such as ATP, and in situations when a fourth amplitude value, distinct from those in the paced chambers, is needed, such as during higher-amplitude backup pacing during pacing threshold tests. For single or dual chamber devices, fewer than four hold capacitors may be used. Additionally, the positive connectors of Chold 104 may be connected to VSS and Bplus via switches not explicitly shown in FIG. 5A.

The support capacitor may be configured to pace to any other chamber through the switch matrix. One purpose for the support capacitor is that during RV capture management, IMD 16 can pace off the support capacitor through the RV leads for 3 paces, then a test pace of the RV hold capacitor, followed by a backup pace off the support capacitor. One purpose of the sequence is to have the support voltage be high enough to guarantee capture of the heart tissue, while the test pace amplitude is varied during the capture routine to determine the voltage at which capture occurs or is lost. The purpose of the backup pace is to capture the heart if the test pace did not. If the test pace did capture the heart, the backup pace is occurring during the refractory interval, so it does not capture the heart muscle or start another pace.

FIG. 6 shows a table showing the k-factors for each of the charge and pump modes and the corresponding switch closures for charge pump 100 of FIG. 5A. In the table of FIG. 6, an X means that the switch of the corresponding column is closed when implementing the mode of corresponding row. The fraction in the mode name represents the K factor for that mode. For example, pump mode A ½× corresponds to a pump mode A with a K factor of ½. As another example, pump mode B 4× corresponds to a pump mode B with a K factor of 4.

Charge pump 100 is configured to operate in two main modes, referred to herein as mode A and mode B, with each of the main modes having multiple sub modes, with each sub mode corresponding to a different K factor. Mode A is designed to have more fractional k-factors but a lower maximum multiplier (i.e., 3× in FIG. 6). Mode B has a higher maximum multiplier (4× in FIG. 6) but fewer fractional values. While mode A may generally offer improved battery life, some patients may require mode B if one of their four heart chambers requires the ⅞× or 4× K factor in order to provide a sufficient pacing voltage.

Charge pump 100 can also operate in a direct mode (CM_1×) that is implemented by a separate set of switches that charge the hold capacitor directly from BPLUS. As the charge pumps are shared between the pacing hold capacitors, the charge modes are mutually exclusive, that is, all pacing hold cap charging must be done in the same charge mode and the k-factors must be selected from that charge mode. Switching between charge modes A and B on a chamber by chamber basis may waste current due to charge transfer that occurs switching between charge modes, as the voltage on the pump capacitors may need to change at a high rate.

As a further note on charge modes, all charge mode A modes are compatible, so that if one cap needs a ¾× k-factor and another needs a ⅝× k-factor, the charge pumps do not drain extra current. In addition, the 1× charge mode can be used with either charge mode A or charge mode B.

Charge pump 100 operates in conjunction with the Pacing Outputs capDAC amplitude comparator to pump and monitor the voltage on the hold capacitors. During the initial pumping time, charge pump 100 may be in "fast" mode (e.g., 2 kHz or 8 kHz pump clock) until all the hold capacitor voltages are met. Then, charge pump 100 may go into a maintenance mode (e.g., 256 Hz pump clock) to maintain the voltage.

The purpose of the pacing charge pumps is to efficiently generate a regulated voltage on the pacing hold capacitors which are then used to deliver (current) energy to the heart via the output circuit switches. The pacing charge pumps may comprise a capacitive charge pump shown in FIG. 5A which is used to generate voltages proportional to the battery voltage, the 1× charge and discharge switches and the pace amplitude comparator. The pace amplitude comparator indicates when the hold capacitor is fully charged so the charge pumps get shut off to prevent putting too much voltage on the hold capacitor. The pacing charge pumps are multiplexed between 4 hold capacitors (LVchold, Achold, RVchold, and Schold) which can all be programmed to different pace amplitudes.

Charge pump 100 is configured to operate in both charge modes and pump modes. The charge mode corresponds to the first phase where the switch across the battery is closed to the hold capacitor. The pump mode corresponds to the second phase where the pump cap is connected to the hold capacitor.

FIG. 5A shows the charge pumps switch matrix structure. Note that Chold represents one or more, e.g., four, hold capacitors, and any switch that connects to it represents one or more, e.g., four, switches between a common node and the corresponding hold capacitor: Atrial (A), Right Ventricular (RV), Left Ventricular (LV) and Support (S). FIG. 6 shows the kfactors for each of the charge and pump modes and the corresponding switch closures. CP1 to CP4 represent the 4 pacing charge pump capacitors. In one implementation of charge pump 100, CP1-CP3 have capacitances of 100 nF, and CP4 had a capacitance of 470 nF, although numerous of capacitance values may also be used.

The base switching clock for the pacing charge pumps can be referred to as CP_CLK. The charge phase of the circuit is in phase with CP_CLK and the pump phase is out of phase with CP_CLK. A non-overlap clock generator is used to create non-overlapping CHG and PMP signals from CP_CLK. The non-overlap prevents crowbar current between BPLUS and VSS (e.g., ground) through the charge pump switches. While the frequency of the clock may not be specified, each duty cycle phase typically needs to be of enough duration to transfer the entire charge through each phase. The frequency needs to be great enough to complete the entire charge transfer. Also, the voltage driving the switches needs to be greater than the pump or hold voltages to ensure the switch function with minimal switch impedance. The pump frequency can be adjusted to provide higher rate and higher voltage therapies such as ATP. ATP usually requires maximum pacing energy that is fundamentally limited by battery output impedance, switch impedances, and charge transfer durations.

The signal names in the table of FIG. 6 designate the switch being closed and whether it is being used in the charge or pump mode. For instance, S4C denotes the control for pacing charge pumps switch 4 in charge mode. The switch control signals are ANDed with the corresponding CHG or PMP signal. If a switch can be active in either charge or pump mode, the ANDed signals are ORed together to drive the switch control signal. Note that the OR of the AND can be accomplished using only NAND gates as a DeMorgan equivalent function.

Controlling the switches in this fashion allows setting both the charge and pump modes and only toggling CP_CLK during a set of charging interval for a hold capacitor. Due to the non-overlap clock, the switches function in a "break-before-make" mode so that there is a short time when all switches are open as the transition from charge to pump and pump to charge modes occurs. All switch drive signals are level shifted to drive the final MOSFET switches.

Figure 5B:
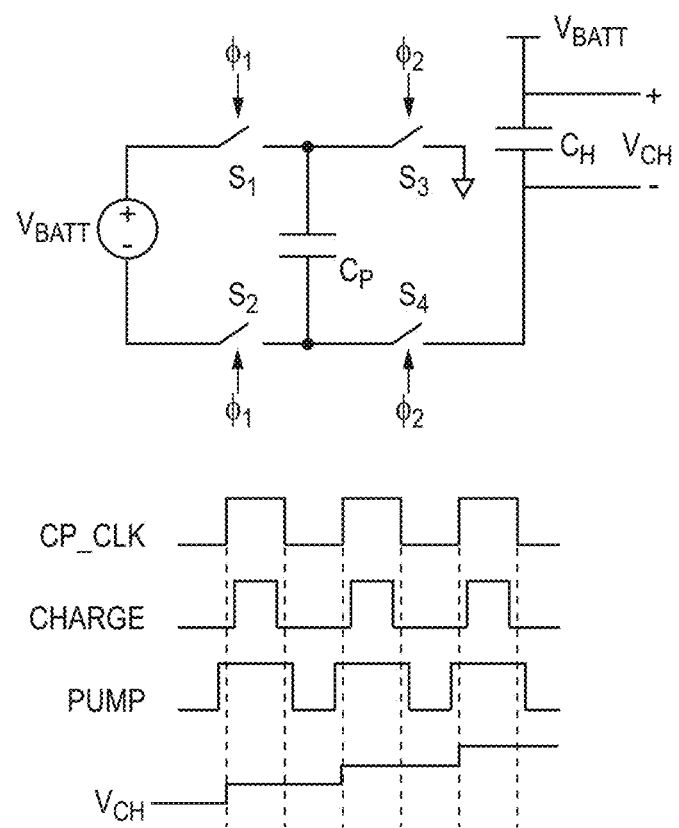
FIG. 5B shows an example of the operation of charge pumps and non-overlap pump phases.

FIG. 5B shows an example of the operation of charge pumps and non-overlap pump phases. FIG. 5B shows an example of creating a 2× voltage on the hold capacitor Ch. During phase 1 (F 1), S1 and S2 are closed which connects Cp from Vbatt to ground. During Phase 2 (F2), S3 and S4 are closed, which transfers charge to Ch. The maximum voltage (Vch) that can be developed is twice the battery voltage.

The clock phases Phi 1 and Phi 2 cannot be active at the same time, so they are implemented as non-overlapping clocks. Below the circuit diagram in FIG. 5B, the clock CP_CLK is used to generate CHARGE (CHG) and PUMP (PMP). The CHARGE phase corresponds to PHI 1 and the PUMP phase corresponds to PHI 2. FIG. 5B also shows how the voltage on Chold (measured across the capacitor) increases as the charge is transferred from the pump cap to the hold cap. The time constant on each step is due to the effective capacitance and the resistance of the switches. When there is little voltage across Ch, the steps are the largest since nearly all of the charge transfers out of Cp to Ch. As Ch increases, less charge transfers and the step size decreases. This gets into the quantization step size in the description. If hundreds of steps are put together, each one decreasing in size, the overall envelope looks like a stairstepped version of an R-C charge curve, with the R being a function of the effective pump capacitance and frequency (which is all the taus that are in the description).

Figure 7A:
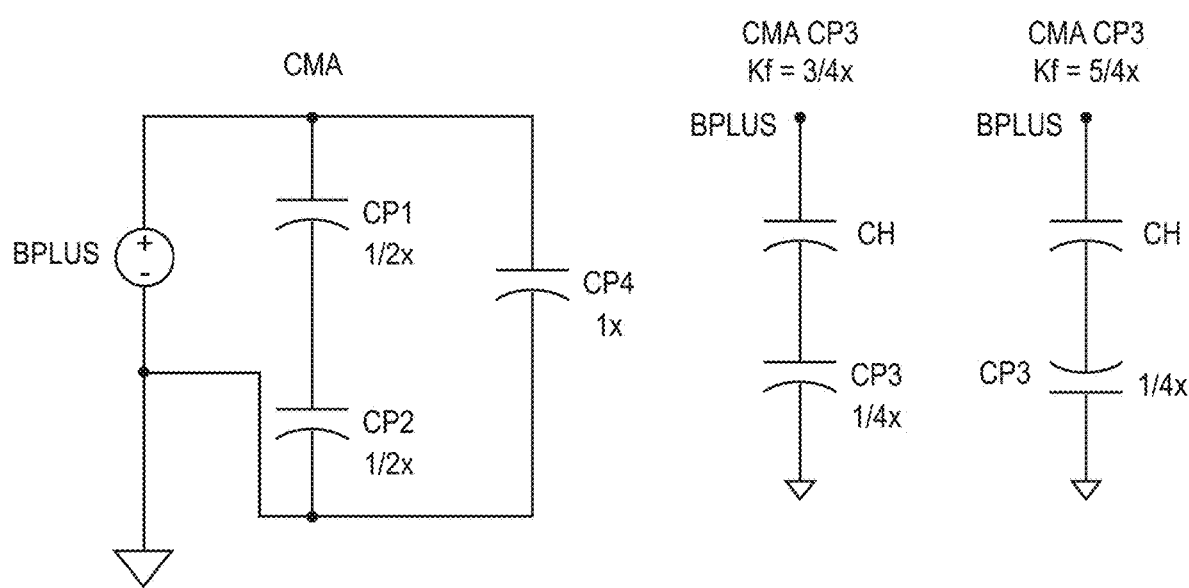
FIGS. 7A-7P illustrate different switch configurations for the various modes that the charge pump of FIG. 5A may be configured to implement.
Figure 7B:
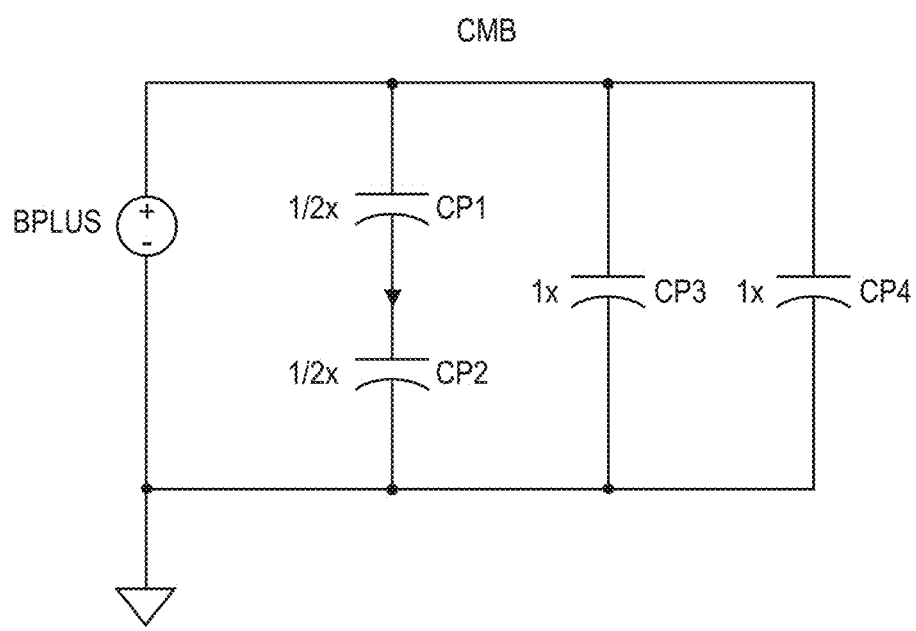
Figure 7C:
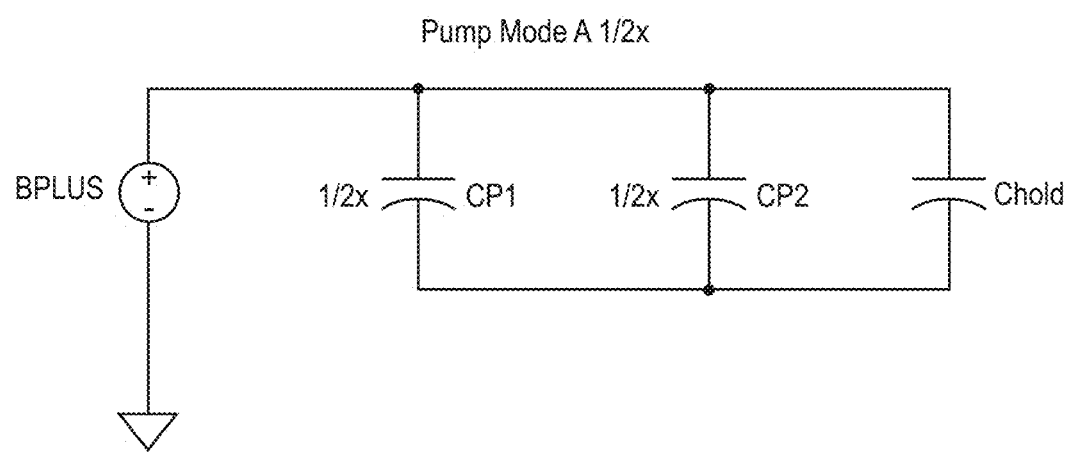
Figure 7D:
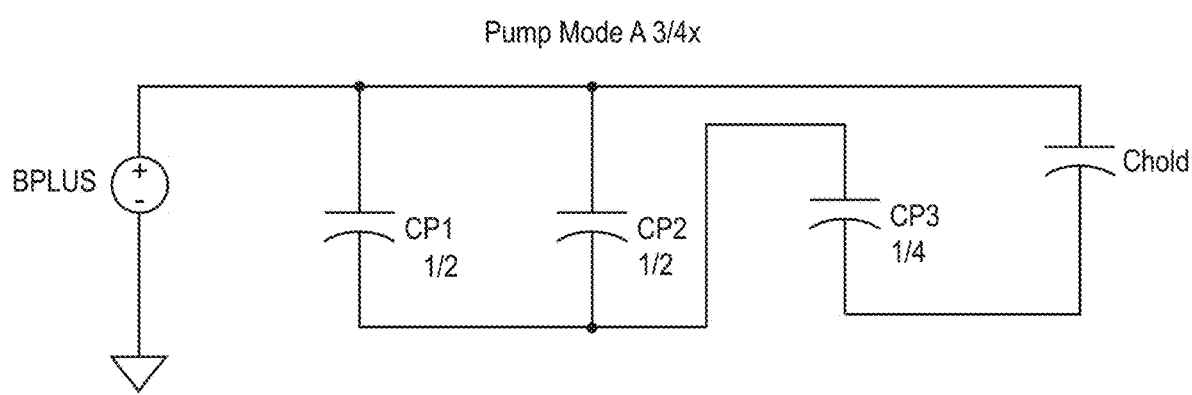
Figure 7E:
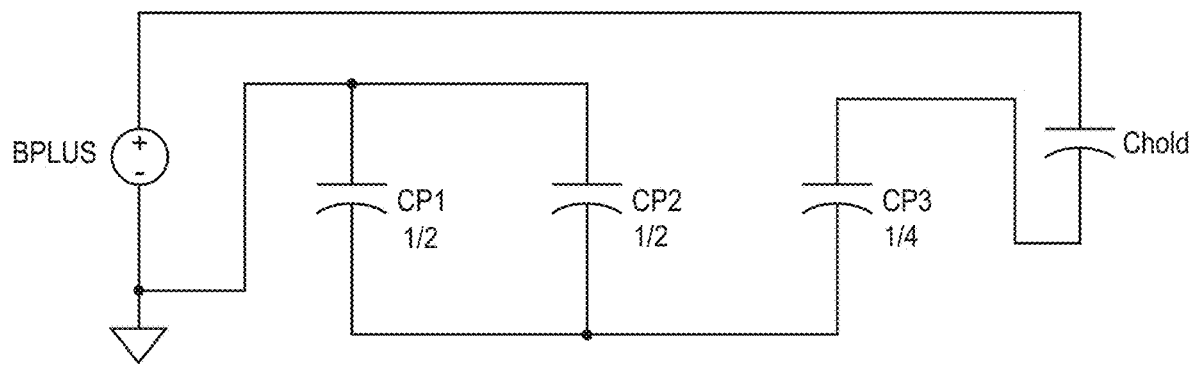
Figure 7F:
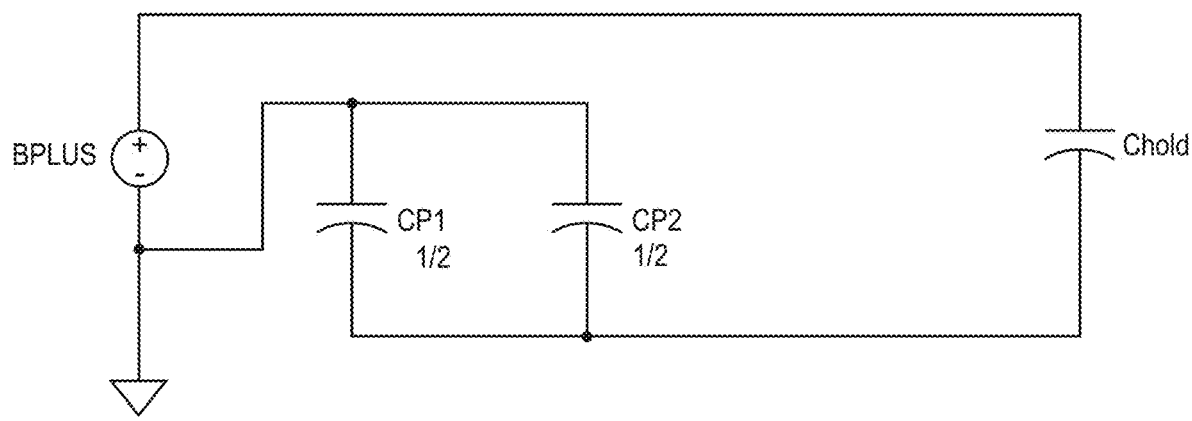
Figure 7G:
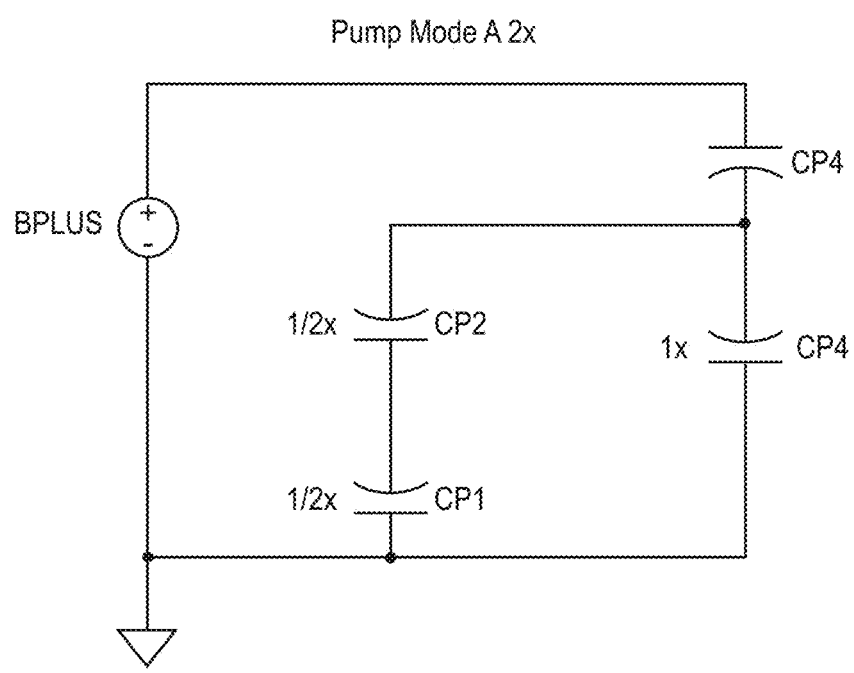
Figure 7H:
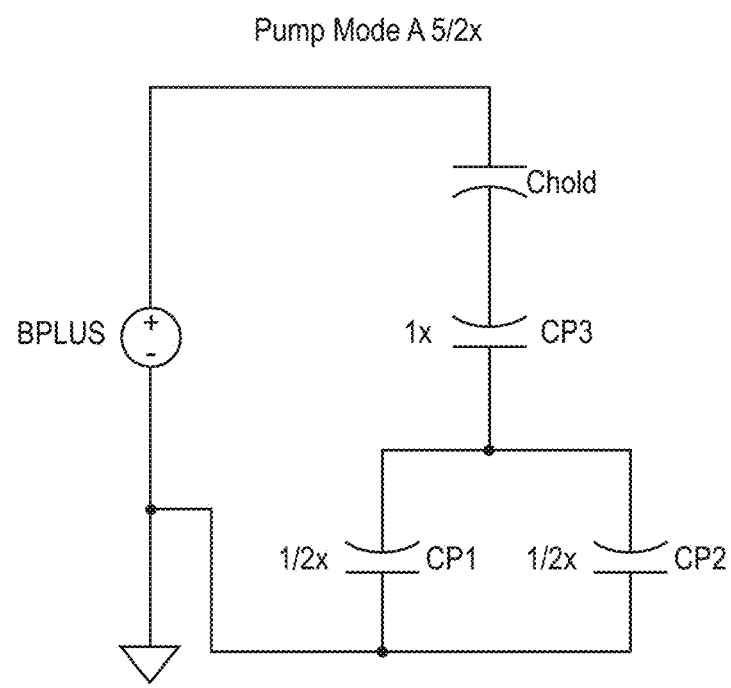
Figure 7I:
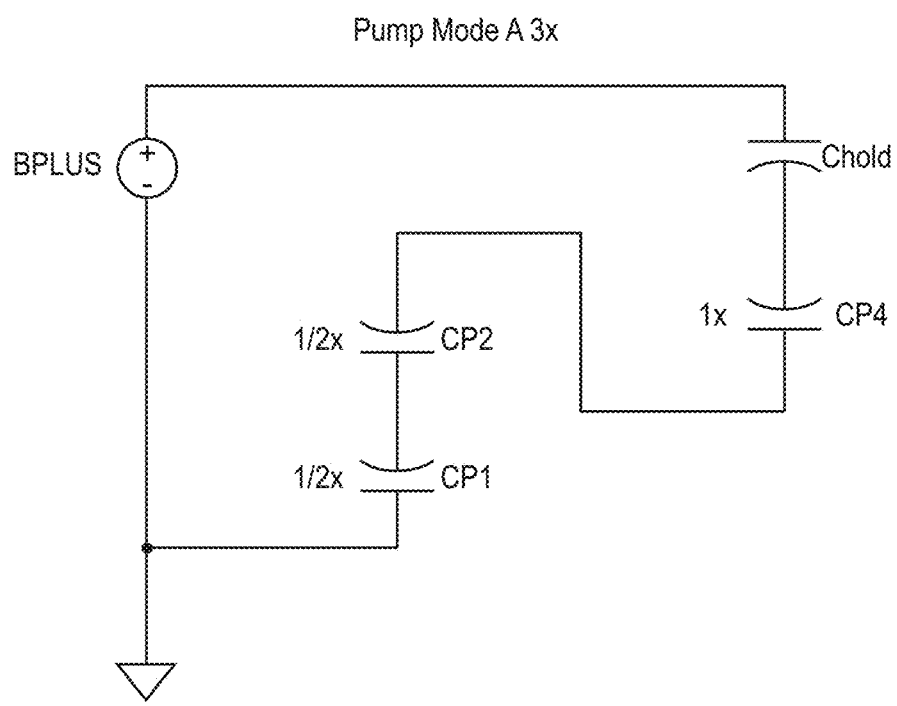
Figure 7J:
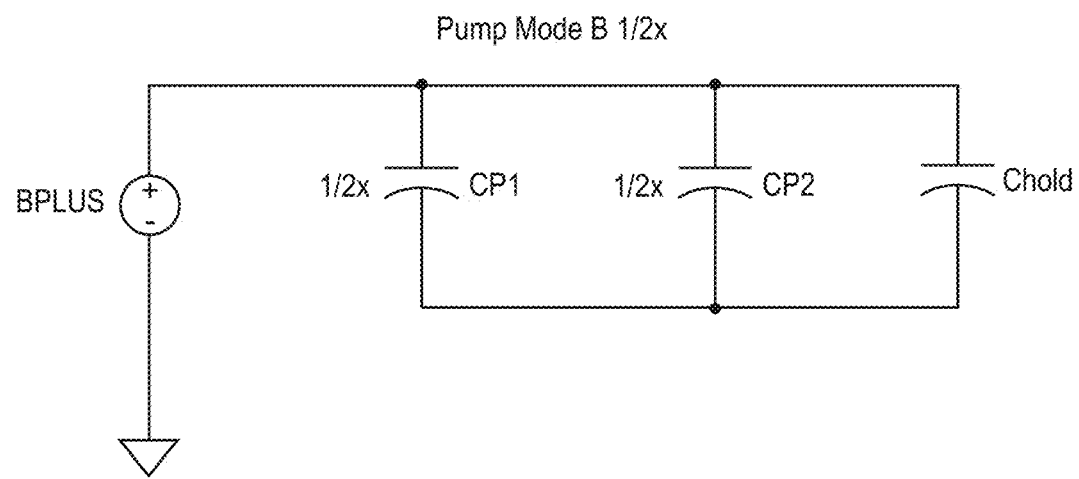
Figure 7K:
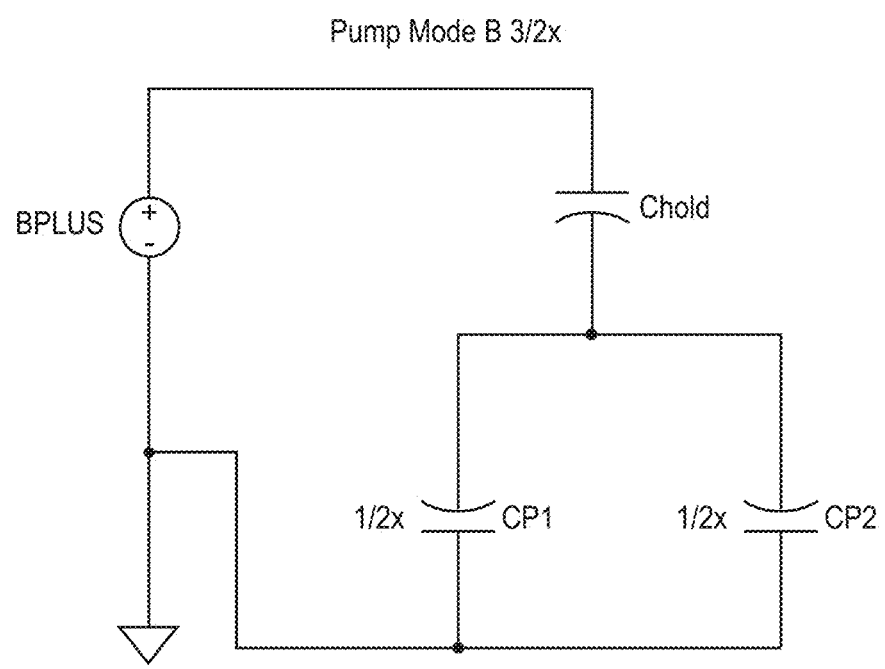
Figure 7L:
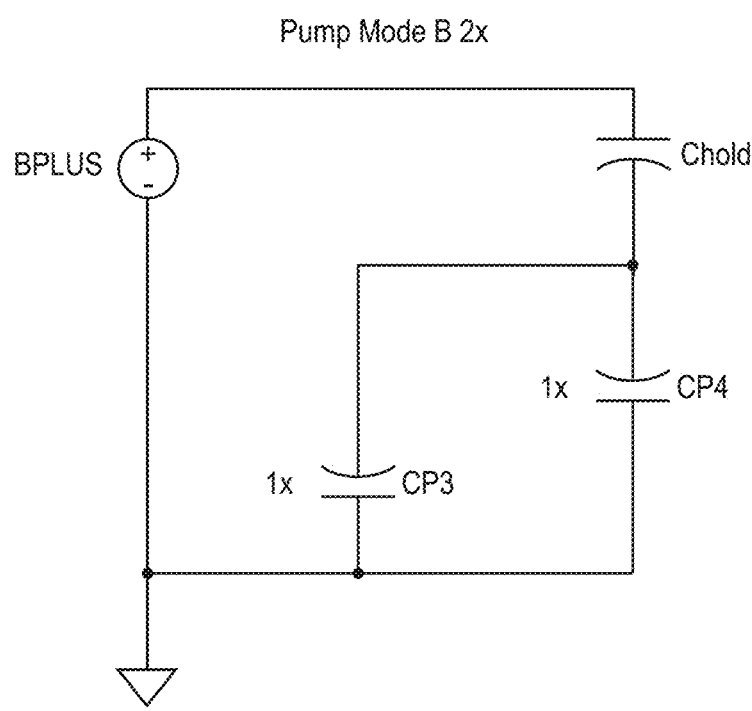
Figure 7M:
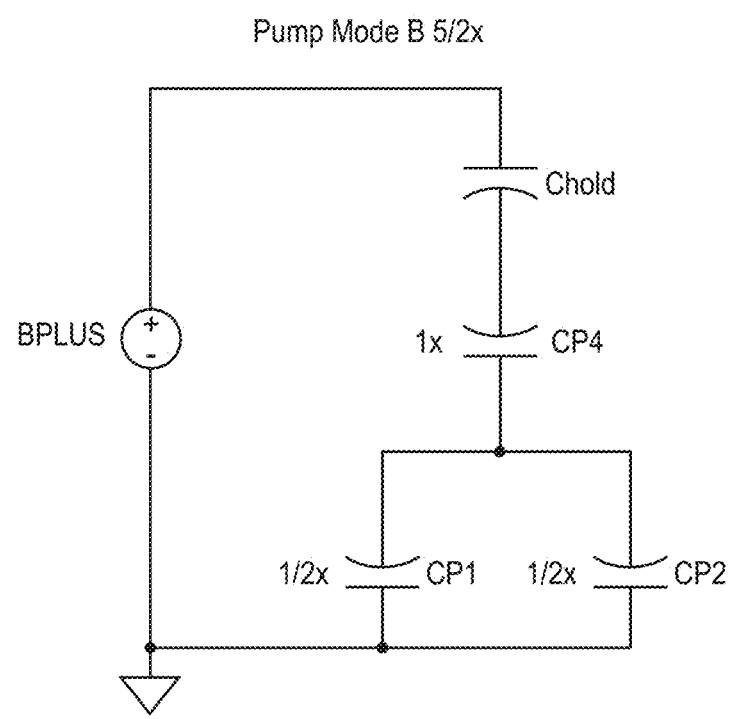
Figure 7N:
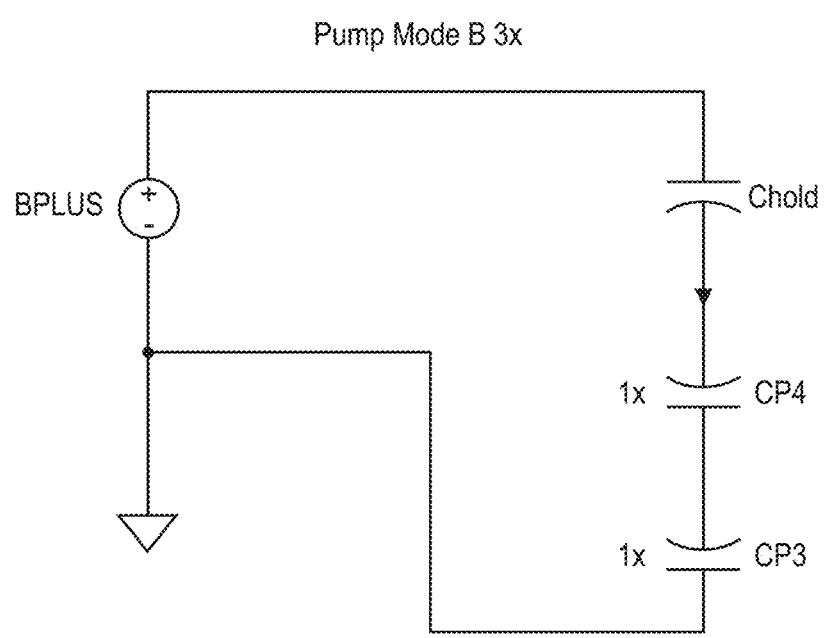
Figure 7O:
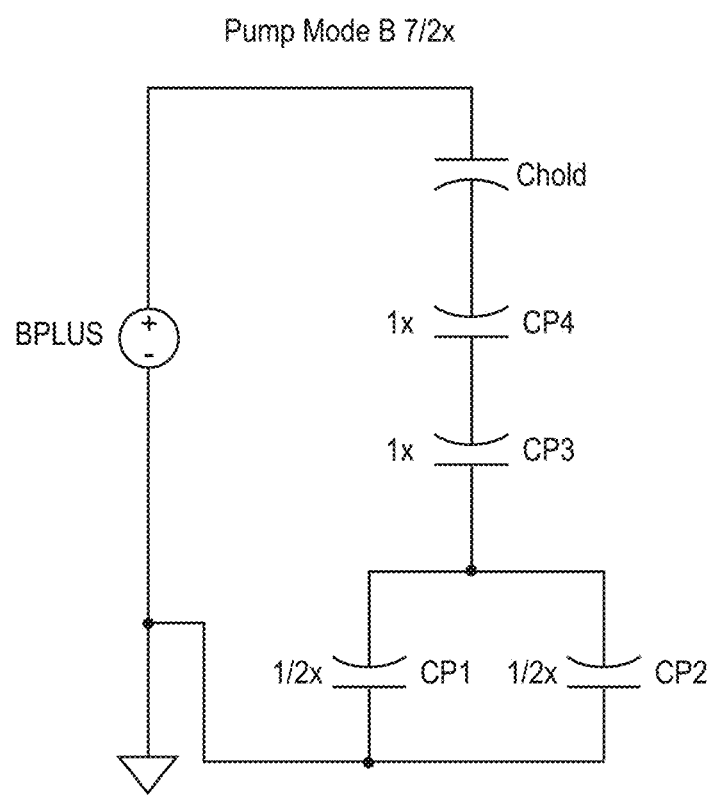
Figure 7P:
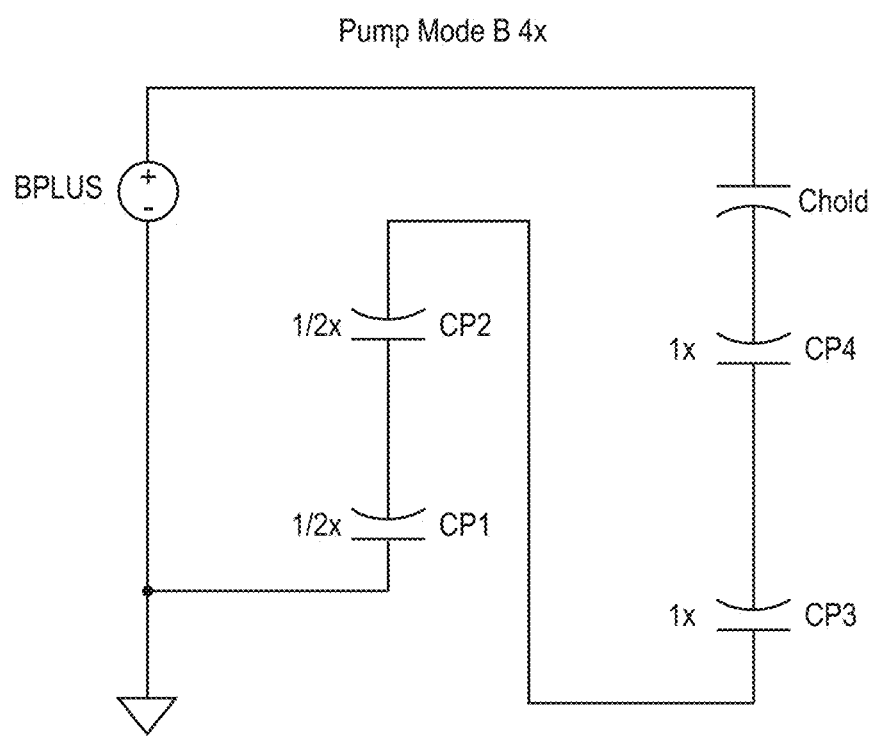

FIGS. 7A-7P illustrate the various modes that charge pump 100 may be configured to implement. In other words, FIGS. 7A-7P illustrate the operation of charge pump 100 with different switch configurations corresponding to different modes.

During the time the hold capacitor is not being used to deliver a pace, the top plate of the hold capacitor is tied to BPLUS thru a low impedance switch, approximately 5 to 20 ohms. The 1× charge pump mode "pumps" the hold capacitor using a PMOS FET switch connected in series between the hold cap bottom plate and VSS. The 1× series charge switches were sized for each charge pump operating clock frequency (256 Hz, 2048 Hz, and 8192 Hz) such that the quantization errors at each frequency were similar to the previous Brady platforms which have the Capture Management features. The charging time constant is hold capacitor times the effective switch impedance. The effective switch impedance is the switch "on" impedance divided by the switch duty cycle. For a 50% duty cycle the effective switch impedance is 2× the switch on impedance.

FIG. 7A is a functional diagram illustrating the operation of charge pump 100 when the switches of charge pump 100 are set (i.e., opened or closed) to implement charge mode A. In charge mode A (e.g., FIG. 7A), CP1 and CP2 are connected in series across BPLUS, charging to ½Bplus across each capacitor. CP4 is connected across BPLUS for a full 1× Bplus during charging. CP3 is only used for CMA_3_4× (0.75×) and CMA_5_4_× (1.25×) pump modes in Mode A, so for those pump modes CP3 is connected to the hold capacitor as shown in FIG. 7A. When the voltage on the hold capacitor is near zero, CP3 quickly charges to nearly the full Bplus voltage since it is 100× lower capacitance than the hold capacitors. As the hold capacitor charges, CP3 charges to a lower voltage until it is ¼× Bplus at steady state. For other charge mode A configurations, CP3 is not used.

FIG. 7B is a functional diagram illustrating the operation of charge pump 100 when the switches of charge pump 100 are set to implement charge mode B. In charge mode B, CP1 and CP2 are connected in series across BPLUS, charging to ½Bplus across each capacitor. CP3 and CP4 are connected across BPLUS for a full 1× Bplus during charging.

FIG. 7C is a functional diagram illustrating the operation of charge pump 100 when the switches of charge pump 100 are set to implement charge mode A ½×. For the CMA ½× pump mode, CP1 and CP2 are connected in parallel to the hold capacitor as shown in FIG. C. The estimated hold capacitor voltage is shown by equation 3 below.

$$V_{final} = \left(((0.5 \cdot Bplus) - V_{initial})\left(1 - e^{\frac{-t}{\tau}}\right)\right) + V_{initial} \quad (3)$$

$$\tau = C_{hold} \cdot \frac{1}{(freq \cdot (CP1 + CP2))}$$

FIG. 7D is a functional diagram illustrating the operation of charge pump 100 when the switches of charge pump 100 are set to implement pump mode A ¾×. For the CMA ¾× pump mode, CP1 and CP2 are connected in parallel and in series with CP3 across the hold capacitor as shown in FIG. 7D. The estimated hold capacitor voltage is shown by equation 4 below.

$$V_{final} = \left(((0.75 \cdot Bplus) - V_{initial})(1 - e^{\frac{-t}{\tau}})\right) + V_{initial} \quad (4)$$

$$\tau = C_{hold} \cdot \frac{1}{\left(freq \cdot \left(\frac{m}{\frac{1}{CP1 + CP2} + \frac{1}{CP3}}\right)\right)}$$

The factor of "m" in the denominator of the time constant is due to the connection of CP3 to the hold cap during the charge phase that effectively pumps the hold cap during this time. Since the hold cap is "pumped" during both phases, the overall time constant is a combination of the parallel/serial pump capacitors seen in FIG. 7D and CP3 only as seen in FIG. 14, with hold cap charging occurring on both clock phases. As both phases are used, the effective impedance from CP3 is half what it would be for a single phase pump. In some implementations, "m" may be equal to 4.

FIG. 7E is a functional diagram illustrating the operation of charge pump 100 when the switches of charge pump 100 are set to implement pump mode A 5/4×. For the CMA 5/4× pump mode, CP1 and CP2 are connected in parallel and in series with CP3 across the hold capacitor as shown in FIG. 7E. The estimated hold capacitor voltage is shown by equation 5 below.

$$V_{final} = \left(((1.25 \cdot Bplus) - V_{initial})(1 - e^{\frac{-t}{\tau}})\right) + V_{initial} \quad (5)$$

$$\tau = C_{hold} \cdot \frac{1}{\left(freq \cdot \left(\frac{m}{\frac{1}{CP1+CP2} + \frac{1}{CP3}}\right)\right)}$$

The factor "m" in the denominator of the time constant is due to the connection of CP3 to the hold cap during the charge phase that effectively pumps the hold cap during this time. As the hold cap is "pumped" during both phases, the overall time constant is a combination of the parallel/serial pump capacitors seen in FIG. 7D and CP3 only as seen in FIG. 7A, with hold cap charging occurring on both clock phases. As both phases are used, the effective impedance from CP3 is half what it would be for a single phase pump. For this design "m" is 4. The pump phase shows how k-factors greater than 1× reference the pump capacitors to VSS.

For the 3/4× and 5/4× modes described above, the hold capacitor is "pumped" during both the charge and pump phase, or alternatively, the hold capacitor becomes the charging voltage for CP3. This applies to both 3/4× and 5/4×, with only the configuration of CP3 during the charge phase being different. Using a two phase clock enables more pumps per unit time, charging the hold capacitor faster. As the charge pump is shared, fast charging may be desirable, especially as pacing rates increase and the time between paces decreases.

FIG. 7F is a functional diagram illustrating the operation of charge pump 100 when the switches of charge pump 100 are set to implement pump mode A 3/2×. For the CMA 3/2× pump mode, CP1 and CP2 are connected in parallel to the hold capacitor as shown in FIG. 7F. The estimated hold capacitor voltage is shown by equation 6 below.

$$V_{final} = \left(((1.5 \cdot Bplus) - V_{initial})(1 - e^{\frac{-t}{\tau}})\right) + V_{initial} \quad (6)$$

$$\tau = C_{hold} \cdot \frac{1}{(freq \cdot (CP1 + CP2))}$$

FIG. 7G is a functional diagram illustrating the operation of charge pump 100 when the switches of charge pump 100 are set to implement pump mode A 2×. For the CMA 2× pump mode, the series combination of CP1 and CP2 in parallel with CP4 is connected to the hold capacitor as shown in FIG. 7G. The estimated hold capacitor voltage is shown by equation 7 below.

$$\tau = C_{hold} \cdot \frac{1}{\left(freq \cdot \left(\frac{CP1 \cdot CP2}{CP1 + CP2} + CP4\right)\right)} \quad (7)$$

$$V_{final} = \left(((2 \cdot Bplus) - V_{initial})(1 - e^{\frac{-t}{\tau}})\right) + V_{initial}$$

FIG. 7H is a functional diagram illustrating the operation of charge pump 100 when the switches of charge pump 100 are set to implement pump mode A 5/2×. For the CMA 5/2× pump mode, the parallel combination of CP1 and CP2 in series with CP3 is connected to the hold capacitor as shown in FIG. 7H. The estimated hold capacitor voltage is shown by equation 8 below.

$$V_{final} = \left(((2.5 \cdot Bplus) - V_{initial})(1 - e^{\frac{-t}{\tau}})\right) + V_{initial} \quad (8)$$

$$\tau = C_{hold} \cdot \frac{1}{\left(freq \cdot \left(\frac{(CP1+CP2)CP3}{CP1+CP2+CP3}\right)\right)}$$

FIG. 7I is a functional diagram illustrating the operation of charge pump 100 when the switches of charge pump 100 are set to implement pump mode A 3×. For the CMA 3× pump mode, the series combination of CP1, CP2 and CP3 is connected to the hold capacitor as shown in FIG. 7I. The estimated hold capacitor voltage is shown by equation 9.

$$V_{final} = \left(((3 \cdot Bplus) - V_{initial})(1 - e^{\frac{-t}{\tau}})\right) + V_{initial} \quad (9)$$

$$\tau = C_{hold} \cdot \frac{1}{\left(freq \cdot \left(\frac{1}{\frac{1}{CP1} + \frac{1}{CP2} + \frac{1}{CP3}}\right)\right)}$$

FIG. 7J is a functional diagram illustrating the operation of charge pump 100 when the switches of charge pump 100 are set to implement pump mode B 1/2×. For the CMB 1/2× pump mode, CP1 and CP2 are connected in parallel to the hold capacitor as shown in FIG. 7J. The estimated hold capacitor voltage is shown in equation 10 below.

$$V_{final} = \left(((0.5 \cdot Bplus) - V_{initial})(1 - e^{\frac{-t}{\tau}})\right) + V_{initial} \quad (10)$$

$$\tau = C_{hold} \cdot \frac{1}{(freq \cdot (CP1 + CP2))}$$

FIG. 7K is a functional diagram illustrating the operation of charge pump 100 when the switches of charge pump 100 are set to implement pump mode B 3/2×. For the CMB 3/2× pump mode, CP1 and CP2 are connected in parallel to the hold capacitor as shown in FIG. 7K. The estimated hold capacitor voltage is shown by equation 11 below.

$$V_{final} = \left(((1.5 \cdot Bplus) - V_{initial})(1 - e^{\frac{-t}{\tau}})\right) + V_{initial} \quad (11)$$

$$\tau = C_{hold} \cdot \frac{1}{(freq \cdot (CP1 + CP2))}$$

FIG. 7L is a functional diagram illustrating the operation of charge pump 100 when the switches of charge pump 100 are set to implement pump mode B 2×. For the CMB 2× pump mode, CP3 and CP4 are connected in parallel to the hold capacitor as shown in FIG. 7L. The estimated hold capacitor voltage is shown by equation 12 below.

$$V_{final} = \left(\left((2 \cdot Bplus) - V_{initial}\right)\left(1 - e^{\frac{-t}{\tau}}\right)\right) + V_{initial} \quad (12)$$

$$\tau = C_{hold} \cdot \frac{1}{(freq \cdot (CP3 + CP4))}$$

FIG. 7M is a functional diagram illustrating the operation of charge pump 100 when the switches of charge pump 100 are set to implement pump mode B 5/2×. For the CMB 5/2× pump mode, the parallel combination of CP1 and CP2 in series with CP4 is connected to the hold capacitor as shown in FIG. 7M. The estimated hold capacitor voltage is shown by equation 13 below.

$$V_{final} = \left(\left((2.5 \cdot Bplus) - V_{initial}\right)\left(1 - e^{\frac{-t}{\tau}}\right)\right) + V_{initial} \quad (13)$$

$$\tau = C_{hold} \cdot \frac{1}{\left(freq \cdot \left(\frac{(CP1 + CP2)CP4}{CP1 + CP2 + CP4}\right)\right)}$$

FIG. 7N is a functional diagram illustrating the operation of charge pump 100 when the switches of charge pump 100 are set to implement pump mode B 3×. For the CMB 3× pump mode, the series combination of CP3 and CP4 is connected to the hold capacitor as shown in FIG. 7N. The estimated hold capacitor voltage is shown by equation 14 below.

$$V_{final} = \left(\left((3 \cdot Bplus) - V_{initial}\right)\left(1 - e^{\frac{-t}{\tau}}\right)\right) + V_{initial} \quad (14)$$

$$\tau = C_{hold} \cdot \frac{1}{\left(freq \cdot \left(\frac{1}{\frac{1}{CP1} + \frac{1}{CP2} + \frac{1}{CP3}}\right)\right)}$$

FIG. 7O is a functional diagram illustrating the operation of charge pump 100 when the switches of charge pump 100 are set to implement pump mode B 7/2×. For the CMB 7/2× pump mode, the parallel combination of CP1 and CP2 is connected in series with CP3 and CP4 to the hold capacitor as shown in FIG. 7O. The estimated hold capacitor voltage is shown by equation 15 below.

$$V_{final} = \left(\left((3.5 \cdot Bplus) - V_{initial}\right)\left(1 - e^{\frac{-t}{\tau}}\right)\right) + V_{initial} \quad (15)$$

$$\tau = C_{hold} \cdot \frac{1}{\left(freq \cdot \left(\frac{1}{\frac{1}{CP1 + CP2} + \frac{1}{CP3} + \frac{1}{CP4}}\right)\right)}$$

FIG. 7P is a functional diagram illustrating the operation of charge pump 100 when the switches of charge pump 100 are set to implement pump mode B 4×. For the CMB 4× pump mode, the CP1, CP2, CP3 and CP4 are connected in series to the hold capacitor as shown in FIG. 7P. The estimated hold capacitor voltage is shown by equation 16 below.

$$V_{final} = \left(\left((4 \cdot Bplus) - V_{initial}\right)\left(1 - e^{\frac{-t}{\tau}}\right)\right) + V_{initial} \quad (16)$$

$$\tau = C_{hold} \cdot \frac{1}{\left(freq \cdot \left(\frac{1}{\frac{1}{CP1} + \frac{1}{CP2} + \frac{1}{CP3} + \frac{1}{CP4}}\right)\right)}$$

Figure 8:
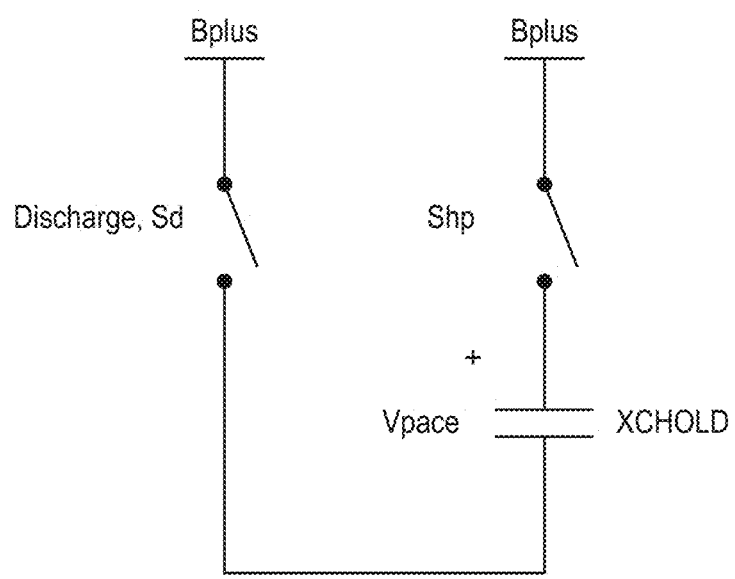
FIG. 8 is a functional datagram illustrating a discharge mode.

FIG. 8 is a functional datagram illustrating a discharge mode. The hold capacitors are sometimes required to be discharged to a lower pace voltage. The hold capacitor is discharged during the normal "pump" window and is continued to be discharged (e.g., Sd and Shp are closed) until the pace amplitude comparator determines that the Chold voltage is at an acceptable voltage level. The discharge switches may be clocked just like the other pump switches so the value can be measured between each discharge "pump."

The magnitude of the voltage step on the pacing hold capacitors due to a "pump" phase may be important since this voltage step is the maximum the hold capacitor should over-shoot its expected pace amplitude target. The pace amplitude comparator measures the hold capacitor while it is not being pumped, specifically the "charging" phase for the pump capacitors, and is expected to be stable in voltage during this measurement and then determines whether an additional pump is required or not based on this measured voltage. Therefore, if the amplitude is just under the required voltage to trip the comparator, the hold capacitor will receive one additional pump prior to the target amplitude being reached. The expected quantization voltage for each K factor setting is determined by equation 17 below.

$$\text{Quantization} = \left(\frac{C_{pump}}{C_{pump} + C_{hold}}\right)\left(((M)(V_{bplus})) - V_{chold}\right) \quad (17)$$

Where:

$C_{pump}$ = effective pump capacitance for the charge pump $k$-factor setting (see time constants in $k$-factor description, multiplier of freq in the denominator is the effective pump capacitance)

$C_{hold}$ = pacing hold capacitance.

$M$ = pacing $k$-factor multiplier $V_{bplus}$ = battery voltage.

$V_{chold}$ = pacing hold capacitor voltage prior to being "pumped".

The worst-case quantization step occurs at the minimum pace amplitude setting for a specific k-factor.

One potential design goal for the pacing charge pump switches is to be low enough impedance so that the voltages during the charge and pump phases have settled during the charge or pump interval. This means that any impedance or time constant calculations can be based on the capacitor values and clock frequency only without having to account for incomplete charge transfer. The individual switches are grouped below by implementation and identified according to switch number as noted in FIG. 5A.

Switches S1, S15 and 519 connect charge pump capacitors to Bplus. Switches S2, S6, S9, S13, S16, and S18 connect charge pump capacitors to VSS. These switches may, for example, be comprised of large HV PMOS switches whose gates are driven to BPLUS to turn off and N3VDD to turn on. During ATP boost mode, where pacing pulse amplitude and/or rate may be increased, another large PMOS switch is turned on in parallel to lower the switching impedance.

Switches S3, S4, S5, S10, S11, S14 and S20 connect charge pump capacitors to each other. The switch is an array of ballasted NMOS switch elements (same as the pacing switch elements) which is turned on by driving ifs gate voltage to the BPLUS/VDD supply voltage and turned off by driving its gate voltage to the lower of N3VDD or the well of the switch element. The well itself uses the well switching feature of the switch element to select the lowest voltage of the switch terminals. During ATP boost mode another switch element is turned on in parallel to lower the switching impedance.

Switches S7, S8, S12, and S17 connect charge pump capacitors to the hold capacitors. At each switch position shown in FIG. 5A there is a separate switch for each of the hold capacitors. For example, S7 connects the CP2 bottom plate to the bottom plate of the hold capacitor. The individual switches are designated by the hold capacitor they connect to, such as S7A, S7RV, S7LV and S7S for atrial, right ventricular, left ventricular and support hold capacitors respectively.

The switches may use the same configuration as the cross coupling switches. During ATP boost mode another large switch element is turned on in parallel with S17 to lower the switching impedance.

Charge pump 100 may operate in multiple use conditions. Examples of such use conditions are normal pacing, capture management, and high current conditions such as charging, ATP or telemetry. In normal pacing, the goal is to maximize battery longevity by monitoring the battery voltage and optimizing the k-factor selection. For capture management, a greater emphasis is placed on having a high enough margin in the charge pump to meet the target amplitude. In high current conditions, the battery may be pulled down significantly from the nominal measured voltage, so k-factor selection should assume a minimum battery voltage in the k-factor selection. While increasing the margin or k-factor multiplier for capture management and high current conditions may draw more current than the normal pacing optimization, these are short term events, so the increase in battery current is not significant over the life of the device.

One challenge in designing a k-factor selection algorithm is to provide enough of an additional margin between the multiplied battery voltage and the target pacing voltage to account for changes to the battery voltage, pacing switch loss variation, pacing voltage measurement variation, and component process variation. In an "open loop" system with no feedback, this requires increasing the margin which can result in selecting a k-factor higher than necessary and drawing more current.

For the hardware/firmware implementation described in this disclosure, the optimum k-factor is chosen as a function of the battery voltage, the programmed pacing amplitude, and nominal pacing switch loss. The pacing output hardware has added the capability to monitor if the target voltage was met on a pace-by-pace basis. If the target voltage is not met, the pacing hardware sends a "100% not met" interrupt to the firmware selection algorithm, which automatically increments the pacing hardware to the next higher k-factor. This feature compensates for the variations noted previously so that the initial calculated k-factor can target typical rather than worst case values, knowing that the system will select a higher k-factor only if necessary.

To prevent a transient high current event from incrementing a k-factor long term and increasing current drain, the firmware recalculates the optimum k-factor if any pacing amplitude is reprogrammed or after a scheduled battery voltage measurement. After this procedure, the system returns to the pace amplitude monitoring mode.

Charge pump 100 may be configured to periodically adjust K factors, in order to select a battery maximizing K factor. The formula for k-factor selection is given equation (18).

$$Kf \geq \frac{Vpace \times ACF + \text{Margin}}{Vbatt} \quad (18)$$

Vpace represents the programmed pace voltage, and ACF represents the Amplitude Correction Factor (also referred to as the Overcharge Ratio) which compensates for losses in the pacing switch path. Vpace×ACF corresponds to the target voltage for the hold capacitor. Margin is the minimum voltage level above the target voltage where a transition occurs, and Vbatt is the measured battery voltage. Tables 1 and 2 below show the hex values used to encode the k-factors in the pacing outputs K-factor registers. The K-factor encoding is mapped so that the k-factor sequencing can proceed by incrementing the k-factor. The 1× mode is decoded twice: once in mode A and once in Mode B.

| MSIC Increment 3 K-factor Encoding | |
| --- | --- |
| K-factor | Hex Code (4 bits) |
| CMA_1_2x | 0x0h |
| CMA_3_4x | 0x1h |
| CMA_1x | 0x2h |
| CMA_5_4x | 0x3h |
| CMA_3_2x | 0x4h |
| CMA_2x | 0x5h |
| CMA_5_2x | 0x6h |
| CMA_3x | 0x7h |
| CMB_1_2x | 0x8h |
| CMB_1x | 0x9h |
| CMB_3_2x | 0xAh |
| CMB_2x | 0xBh |
| CMB_5_2x | 0xCh |
| CMB_3x | 0xDh |
| CMB_7_2x | 0xEh |
| CMB_4x | 0xFh |

The k-factor selection will also make use of the Pacing Outputs Interrupt or POINT. This interrupt can be activated for pacing amplitude and Active Recharge Ratio monitoring. For pacing amplitude monitoring, the interrupt can be configured to trip after a pace occurs if 90% of the target hold capacitor amplitude was not met (legacy operation) or if 100% of the target amplitude was not met. The 100% not met indicates to the firmware that the charge pump never hit the target voltage by the time a pace occurred, so the pumps never left fast mode. By using the 100% not met interrupt, the pacing charge pumps can essentially "auto-trim" by calculating the optimal k-factor and incrementing to the next value if the interrupt occurs. This allows us to set the margin voltage to 0, since the interrupt and increment loop compensates for any variations in the pacing amplitude comparator over process, voltage and temperature.

Switching between 90% not met and 100% not met is controlled by an interrupt mask register. Setting this bit generates an interrupt if the amplitude comparator DAC (ampDAC) has not detected a 100% complete condition on the chamber being paced. Clearing this bit generates an interrupt if the ampDAC has not detected a 90% complete condition on the chamber being paced.

The ability to determine whether 90% or 100% of the target amplitude was achieved may allow for a system or user tradeoff to be made between maximizing battery efficiency (longevity) and maximizing pacing amplitude accuracy. Also, the wider-tolerance (i.e. 90%) amplitude measurement may be used to trigger fault/exception handling logic so as to exclude the possibility of out-of-spec amplitudes, which might otherwise be able affect operation of sensitive operations such as capture threshold tests.

The k-factor selection algorithm should first attempt to select from Charge Mode A. If any chamber requires jumping to charge mode B due to running out of k-factor capacity (i.e., a k-factor higher than 3× is required), then all chamber k-factors must be recalculated for charge mode B.

In high current conditions and capture management, the battery voltage in the equation is set to the minimum expected voltage rather than using the last measured battery voltage. This will depend on the battery used with the system. With a lithium anode/hybrid $CF_x$+SVO cathode chemistry battery chemistry, a minimum battery voltage of 2.2V can be used to calculate the k-factors. All other parameters of the selection (A mode vs B mode, etc.) remain the same as for regular pacing.

Figure 9:
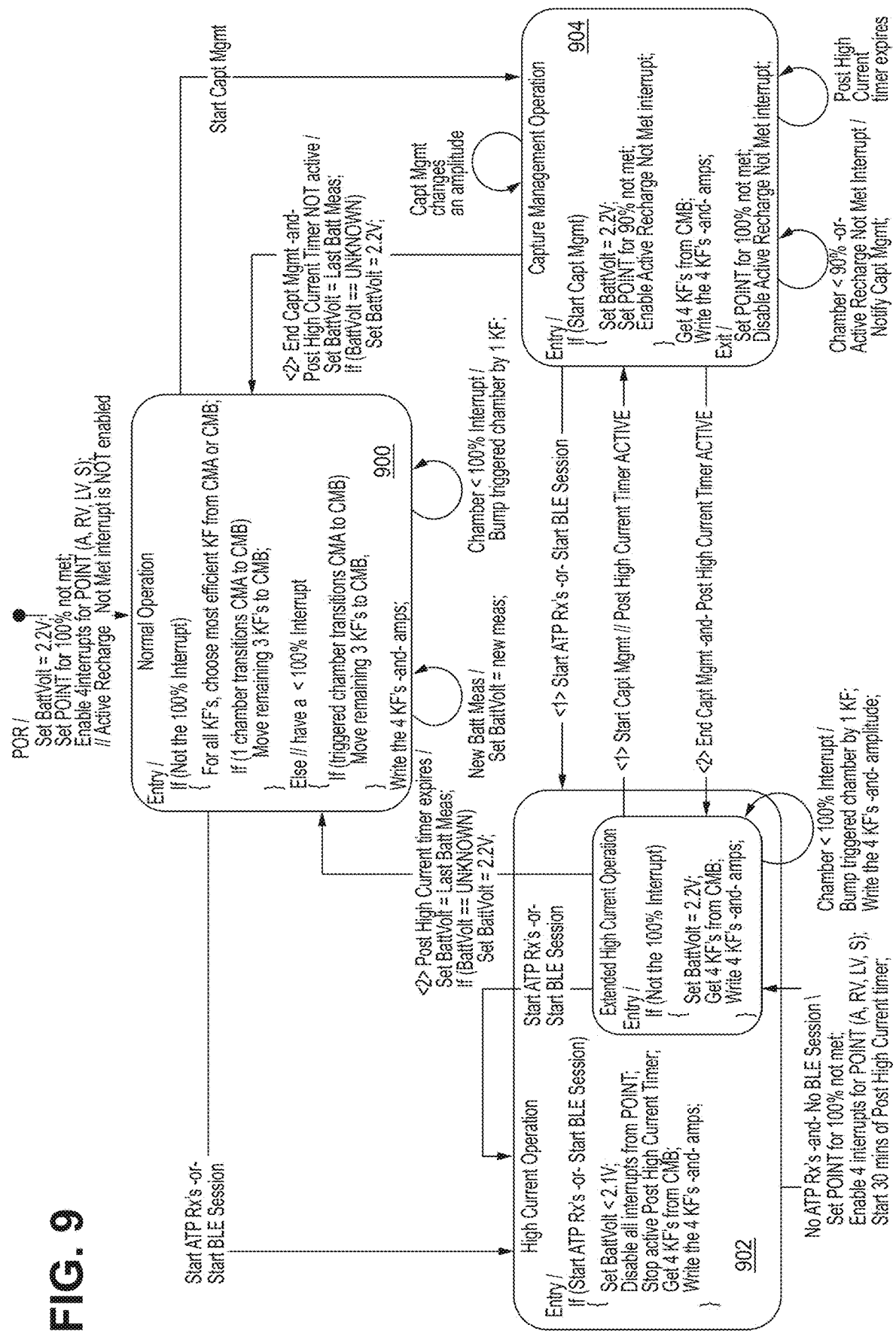
FIG. 9 is a flow diagram that shows an example of an algorithm that may be used for selecting a K factor for a charge pump according to the techniques of this present disclosure.

FIG. 9 shows an example of an algorithm that may be used for selecting a K factor for charge pump 100. The algorithm of FIG. 9 may, for example, be implemented in computer readable instructions (e.g., software or firmware) stored in memory 82 and executed by processor 80. The selection of a K-factor may be, for example, based on the table in FIG. 10. The table of FIG. 10 may be generated from the formula in Equation (18) above, where ACF accounts for the losses in an IPG and the margin=0V. The margin can be set to 0V because of the auto-trim function enabled by the "100% not met" POINT.

Figure 10:
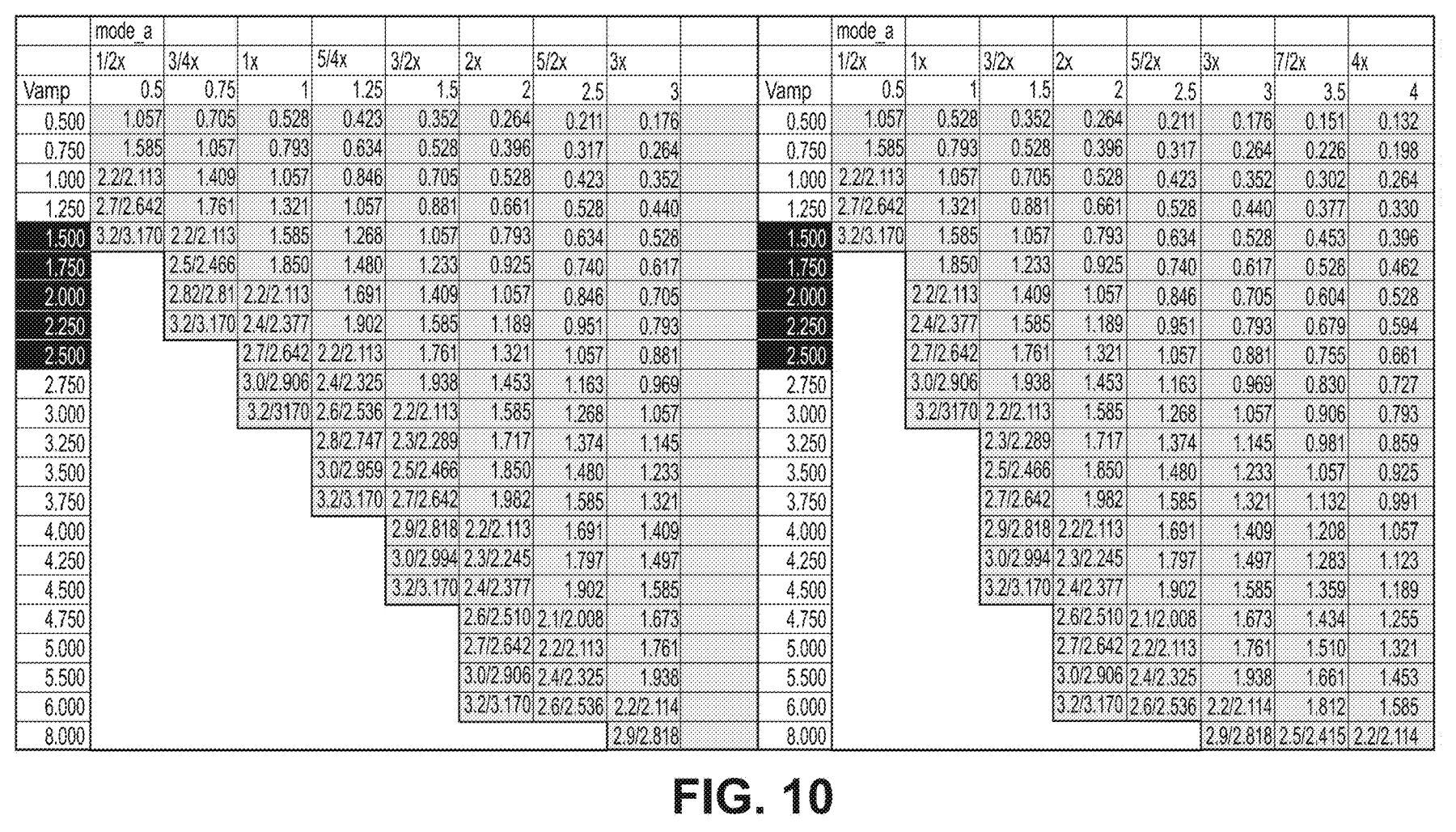

The table of FIG. 10 shows the minimum supply voltage needed for the selected pacing amplitude (Vamp) and k-factor. To limit the size of the lookup table, the pacing amplitude may be limited to the user programmable values, although values can also be calculated on the fly. Any intermediate amplitude that might be accessed during features such as VCM is treated as the next higher user programmable values.

To use the table, the last battery voltage measurement is read. If no battery measurement has yet occurred, such as after a POR, the algorithm uses a default minimum battery voltage of 2.2V. Note that for this algorithm, BattVolt is a variable used by the k-factor algorithm, and can either represent the actual measured battery voltage, or set to a default voltage for special use cases.

For each programmed amplitude, read across the mode_a table from the amplitude and find the smallest k-factor with a supply voltage less than the measured battery voltage. If no mode_a k-factor is found, switch to the mode_b table. Note that all k-factors must be in the same mode table. If any k-factor has to use mode_b, all k-factors must be calculated using the mode_b table.

If the minimum voltage for the selected k-factor is less than 2.2V, no further action will be required until the next amplitude programming or battery measurement, at which point the algorithm recalculates all the k-factors.

Several use cases will now be described. One example use case is normal operation (Auto Trim). In normal operation, the k-factors are recalculated when a battery measurement occurs or when a chamber amplitude is programmed. For each chamber amplitude, the mode_a table is used in conjunction with the battery voltage to determine the k-factor. If any chamber requires a higher k-factor than available in mode_a, then all k-factors must be selected from the mode_b table. The 100% not met interrupt is enabled for all chambers by configuring a register in Processor 80.

When a 100% not met interrupt occurs during normal operation, the k-factor for the chamber that generated the interrupt is incremented to the next higher value. If the k-factor is at the highest mode_a and the interrupt occurs, the mode_b table is used and all chambers are converted to mode_b values. If a chamber reaches the highest mode_b k-factor, no further incrementing occurs.

After a POR, the BattVolt variable is set to 2.2V and k-factors are selected based on this voltage. All other operation in this state is the same as for Normal Operation. Once a valid battery measurement occurs, BattVolt is set to the latest battery voltage and goes to the Normal Operation state. Note that in all use cases if no valid battery measurement is available then BattVolt defaults to 2.2V.

High current operation is defined as the set of use cases that require a larger amount of current. This includes Bluetooth telemetry sessions and ATP. At the start of high current operation, BattVolt is set to the minimum level (less than 2.1V), the pacing interrupt is disabled, and k-factors are selected from mode_b based on this minimum voltage. Once the high current operation completes, the algorithm changes BattVolt to 2.2V, re-enables the pacing interrupts, selects k-factors from the mode_b table and stays in the Extended High Current Operation state until the High Current Timer expires. This allows the battery to recover from the high current operation before reverting to Normal Operation. At the expiration of the High Current Timer, BattVolt reverts back to the last valid battery measurement and Normal Operation resumes.

Upon entering Capture Management Operation, the PO interrupt is set to the 90% not met mode. This is to align with the Capture Management requirement that the delivered pace is at least 90% of the expected value. BattVolt is set to 2.2V and k-factors are selected from the mode_b table based on this voltage. Each time a new test pace amplitude is written, k-factors are recalculated. If a 90% not met interrupt is generated, this is sent to the capture management routine to be managed there. At the end of capture management, BattVolt reverts back to the last valid battery measurement and Normal Operation resumes.

Writing to the following hardware registers affect the operation of the Pacing Outputs pacing charge pump state machine:
PO_A_kf
PO_RV_kf
PO_LV_kf
PO_S_kf
PO_Aamp
PO_RVamp
PO_LVamp
PO_Samp Writing any of these registers triggers the measurement and charging cycle of the charge pump state machine so that it can establish the new value. In this HW implementation, there is an indication that a hold capacitor has been charged to or above a particular level, but no indication if it has fallen below a level. The voltage regulation may be effectively unidirectional. In other words, if the hold capacitor voltage on the cap is not high enough, then the hold capacitor can be pumped up until the target value is met. Once that occurs, IMD 16 may go into maintenance mode checking at a 256 Hz rate. If the cap is too low, the cap can get one pump without repeated checking. On the next 256 Hz interval, the cap can be checked again. However, there may not be a charge pump mode to gradually pump down to prevent from constantly "servoing" up and down trying to find the target value. The discharge mode may be aggressive (e.g., large jumps for each "pump") so as to discharge the cap well below the 100% level.

Due to this measurement capability, when one of the above registers are written, a measurement that shows the level has been met does not indicate whether the hold capacitor was previously charged to a higher voltage and is now well above the new programmed amplitude, or if the hold capacitor is at the proper level for the new programmed value. Therefore, if one of these registers is written and the measure state shows that the voltage has already been met, the hold cap enters the drain mode to pull charge off of the capacitor so that it will approach the final value from below the amplitude measurement trip point.

One of the methods to reduce the effects of soft errors corrupting the hardware registers is to regularly refresh the registers by writing the values. In the case of the PO registers noted here, even writing the same value will trigger a drain/charge sequence, wasting current which affects longevity. To reduce the current drain from a register refresh the following sequence may be followed:

1) Firmware can keep a mirror copy of the hardware amp and kf registers,
2) if any of the four hardware kf registers are different from the firmware mirror, then the four hardware kf registers can be written by the firmware copy,
3) if any of the four hardware amp registers are different from the firmware mirror, then the four HW amp registers will be written by the FW copy.

This difference in the FW and HW comparisons may occur algorithmically according to FIG. 9 or due to the occurrence of a soft error affecting the HW.

During the soft error refresh sequence, the Pacing Outputs amplitude and k-factor registers shall be refreshed only if the value read from the hardware register is different than the value in the corresponding firmware register. This sequence is referred to as a "read before write."

Figure 11:
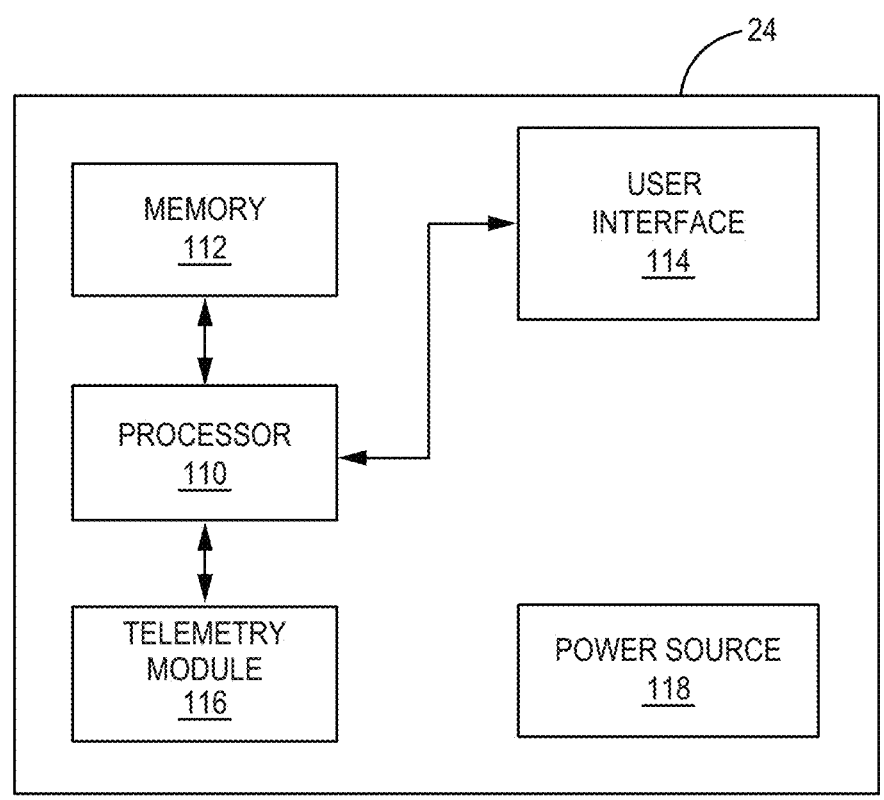
FIG. 11 is a functional block diagram illustrating an example configuration of the programmer of FIG. 1.

In one example implementation, a processor may control a user interface, e.g., user interface 114 of programmer 24 of FIG. 11, to provide a "check box" or some other graphic which may receive input from a user. Using the check box, a clinician may provide input to programmer 24 if undesired muscle and/or nerve stimulation occurred for a particular vector. In other words, the clinician may tag a vector if undesirable muscle and/or nerve stimulation occurred. Providing input in this manner may be allow tagged vectors to be ranked lower than untagged vectors. Tagged vectors may be communicated back to the IMD, e.g., via telemetry circuitry 116 of programmer 24 of FIG. 11, so that the IMD would be able to provided that information to other programmers at later dates, thereby allowing the clinicians the option to exclude vectors with a history of undesired stimulation in future test runs.

In other example implementations, the clinician may specify that only some of the available vectors should be tested. For example, for a quadripolar lead, although there are sixteen possible vectors, a clinician may only be interested in the ten most commonly used vectors, or some other subset of the total available vectors. As such, the clinician may specify, e.g., using programmer 24, the particular vectors that should be tested for pacing capture thresholds.

In some examples, clinicians may save their preferred vectors for a given lead, and then load and run a test using those preferred vectors.

In another example implementation, processor 80 and electrical sensing circuitry 86 may perform impedance measurements for each vector during the pacing capture threshold tests. Processor 80 may control electrical sensing circuitry 86 to perform the impedance measurements tests in parallel with the pacing capture threshold tests. These impedance values may be displayed along with the pacing capture threshold values to the clinician, e.g., via programmer 24, at the end of test.

In one example implementation, a clinician may specify that only vectors having certain qualities, e.g., certain voltages and impedances, should be displayed upon completion of the pacing capture threshold test. For example, a clinician may specify, e.g., using programmer 24, that only vectors having capture thresholds that are less than about 3V and having impedances of less than about 10 ohms should be displayed.

Telemetry circuitry 88 includes any suitable hardware, firmware, software or any combination thereof for communicating with another device, such as programmer 24 (FIG. 1). Under the control of processor 80, telemetry circuitry 88 may receive downlink telemetry from and send uplink telemetry to programmer 24 with the aid of an antenna, which may be internal and/or external. Processor 80 may provide data to be uplinked to programmer 24 and receive data from programmer 24 via telemetry circuitry 88.

FIG. 11 is functional block diagram illustrating an example configuration of programmer 24. As shown in FIG. 11, programmer 24 may include a processor 110, memory 112, user interface 114, telemetry circuitry 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present graphical user interface to a user, and a keypad or another mechanism for receiving input from a user. The user, e.g., a clinician, may define or select vectors to be tested and/or input vector impedance values via user interface 114.

User interface 114 may display the vectors to be tested as well as the results of the pacing capture threshold tests to the clinician. As described above, user interface 114 may display each vector tested, and its associated pacing capture threshold voltage, in some order that the clinician may select or adjust. In some example, the impedance of each tested vector may also be displayed. The results of the tests may also be stored within memory 112.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, Flash memory, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry circuitry 116, which may be coupled to an internal antenna or an external antenna. An external antenna that is coupled to programmer 24 may correspond to the programming head that may be placed over heart 12, as described above with reference to FIG. 1. Telemetry circuitry 116 may be similar to telemetry circuitry 88 of IMD 16 (FIG. 3).

Telemetry circuitry 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, programmer 24 and/or one or more networked computers may enable a user to program aspects of the performance of an implantable medical device in accordance with the techniques described herein.

Figure 12:
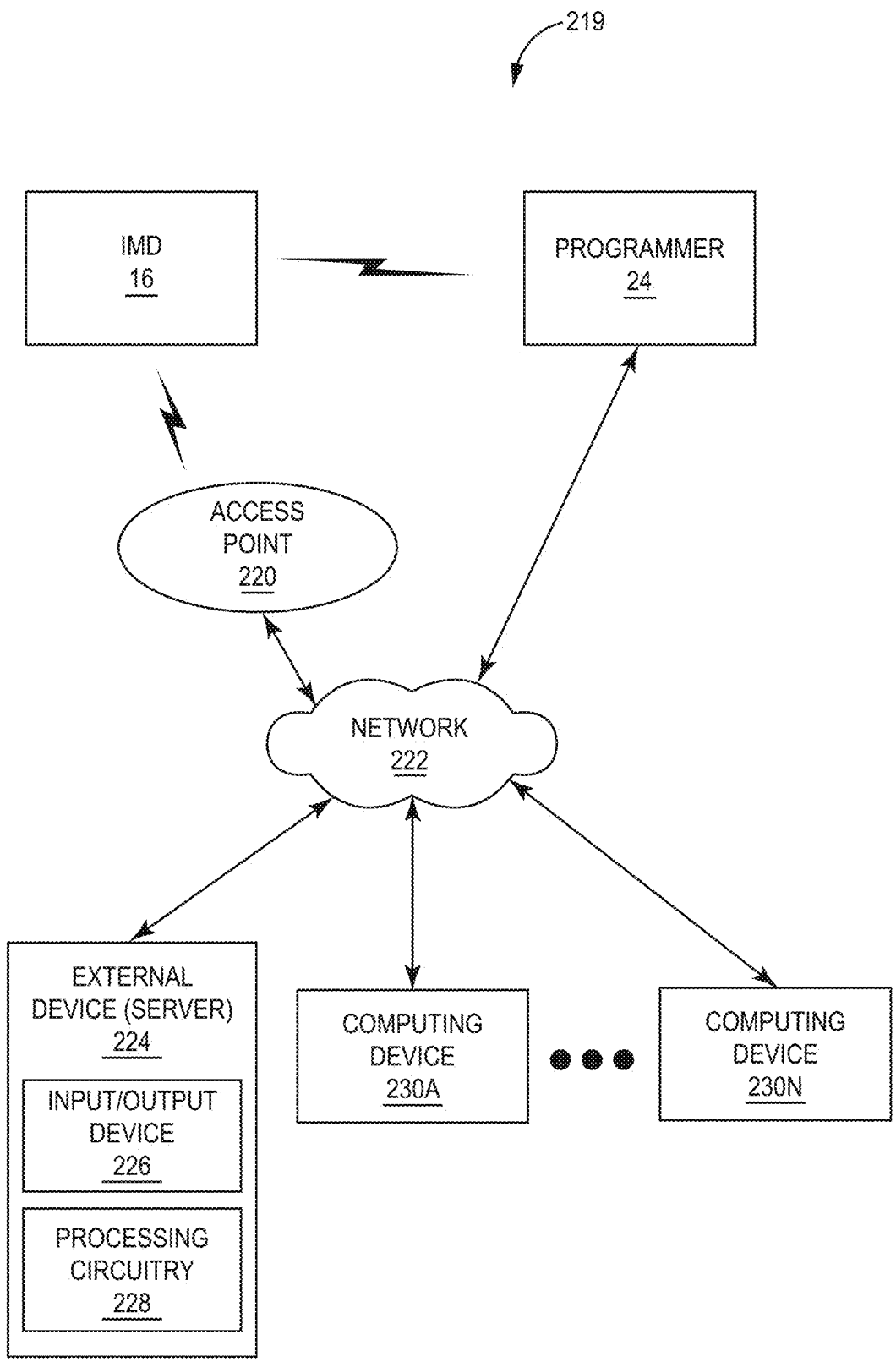
FIG. 12 is a block diagram illustrating an example system that includes a server and one or more computing devices that are coupled to the IMD and the programmer shown in FIG. 1 via a network.

FIG. 12 is a block diagram illustrating an example system 219 that includes an external device, such as a server 224, and one or more computing devices 230A-230N, that are coupled to the IMD 16 and programmer 24 shown in FIG. 1 via a network 222. In this example, IMD 16 may use its telemetry circuitry 88 to communicate with programmer 24 via a first wireless connection, and to communication with an access point 220 via a second wireless connection. In the example of FIG. 12, access point 220, programmer 24, server 224, and computing devices 230A-230N are interconnected, and able to communicate with each other, through network 222. In some cases, one or more of access point 220, programmer 24, server 224, and computing devices 230A-230N may be coupled to network 222 through one or more wireless connections. IMD 16, programmer 24, server 224, and computing devices 230A-230N may each comprise one or more processors, such as one or more microprocessors, DSPs, ASICs, FPGAs, programmable logic circuitry, or the like, that may perform various functions and operations, such as those described herein.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14 and may comprise one or more programming units and/or computing devices (e.g., one or more monitoring units) that may perform various functions and operations described herein. For example, access point 220 may include a home-monitoring unit that is co-located with patient 14 and that may monitor the activity of IMD 16.

In some cases, server 224 may be configured to provide a secure storage site for data that has been collected from IMD 16 and/or programmer 24. Network 222 may comprise a local area network, wide area network, or global network, such as the Internet. In some cases, programmer 24 or server 224 may assemble data in web pages or other documents for viewing by trained professionals, such as clinicians, via viewing terminals associated with computing devices 230A-230N. The illustrated system of FIG. 12 may be implemented, in some aspects, with general network technology and functionality similar to that provided by the Medtronic CareLink® Network developed by Medtronic, Inc., of Minneapolis, Minn.

Various examples of the disclosure have been described. These and other examples are within the scope of the following claims.

The invention claimed is:

1. An implantable medical device (IMD) comprising:
   a battery;
   a hold capacitor configured to deliver an electrical therapy pulse;
   charge pump circuitry configured to transfer energy from the battery to the hold capacitor, wherein the charge pump circuitry comprises;
      a plurality of capacitors; and
      switching circuitry configured to put the charge pump circuitry into a K-factor mode selected from a group of K-factor modes by opening and closing a combination of switches connected to the plurality of capacitors, wherein the group of K-factor modes includes both a plurality of charging modes and a plurality of pumping modes; and
   clocking circuitry configured to:
      generate a pump signal from a clock signal;
      generate a charge signal from the clock signal, wherein the pump signal and the charge signal are non-overlapping signals;
      drive the charge pump circuitry based on the pump signal and the charge signal, wherein the pump signal causes the switching circuitry to put the charge pump circuitry in one of the plurality of charging modes and the charge signal causes the switching circuitry to put the charge pump circuitry in one of the pumping modes.

2. The IMD of claim 1, further comprising one or more memory devices configured to store a K-factor mode lookup table.

3. The IMD of claim 1, further comprising:
   one or more processing circuits configured to:
      determine a voltage of the battery;
      determine a voltage of the electrical therapy pulse;
      based on the determined voltage of the battery and the determined voltage of the electrical therapy pulse, determine a K-factor mode from the group of K-factor modes; and
      cause the switching circuitry of the charge pump circuitry to put the charge pump circuitry into the determined K-factor mode.

4. The IMD of claim 2, further comprising one or more processing circuits, wherein to determine the K-factor mode from the group of K-factor modes, the one or more processing circuits are configured to select the K-factor mode from the K-factor mode look up table.

5. The IMD of claim 1, wherein the first charge mode comprises a 0.75× charge mode.

6. The IMD of claim 1, wherein the second charge mode comprises a 1.25× charge mode.

7. The IMD of claim 1, wherein the charge pump circuitry is configured to operate in a 0.75× pump mode.

8. The IMD of claim 1, wherein the charge pump circuitry is configured to operate in a 1.25× pump mode.

9. The IMD of claim 1, wherein the pump signal causes the switching circuitry to put the charge pump circuitry in one of the plurality of charging modes during a first phase of the clock signal and the charge signal causes the switching circuitry to put the charge pump circuitry in one of the pumping modes during a second phase of the clock signal that is opposite the first phase.

10. An implantable medical device (IMD) comprising:
a battery;
a hold capacitor configured to deliver an electrical therapy pulse; and
charge pump circuitry configured to transfer energy from the battery to the hold capacitor, wherein the charge pump circuitry comprises;
a plurality of capacitors; and
switching circuitry configured to put the charge pump circuitry into a K-factor mode selected from a group of K-factor modes by opening and closing a combination of switches connected to the plurality of capacitors, wherein the group of K-factor modes includes both a plurality of charging modes and a plurality of pumping modes; and
one or more processing circuits configured to:
determine that the IMD has entered a high current mode;
in response to determining that the IMD has entered the high current mode, determine a new K-factor mode from the group of K-factor modes based on a default voltage of the battery; and
cause the switching circuitry of the charge pump circuitry to put the charge pump circuitry into the new K-factor mode.

11. The IMD of claim 10, wherein one or more processing circuits are further configured to:
determine a voltage of the battery;
determine a voltage of the electrical therapy pulse;
based on the determined voltage of the battery and the determined voltage of the electrical therapy pulse, determine a second new K-factor mode from the group of K-factor modes; and
cause the switching circuitry of the charge pump circuitry to put the charge pump circuitry into the determined second new K-factor mode.

12. The IMD of claim 10, wherein the new K-factor mode comprises a 0.75× charge mode.

13. The IMD of claim 10, wherein the new K-factor mode comprises a 1.25× charge mode.

14. The IMD of claim 10, further comprising one or more memory devices configured to store a K-factor mode lookup table.

15. The IMD of claim 14, wherein to determine the K-factor mode from the group of K-factor modes, the one or more processing circuits are configured to select the K-factor mode from the K-factor mode look up table.

16. A method comprising:
putting a plurality of switches into a first switch configuration, wherein the first switch configuration is associated with a first K-factor mode selected from a group of K-factor modes;
transferring, via the plurality of switches in the first switch configuration, energy from a battery to a hold capacitor;
generating a pump signal from a clock signal;
generating a charge signal from the clock signal, wherein the pump signal and the charge signal are non-overlapping signals;
driving charge pump circuitry of an implantable medical device (IMD) based on the pump signal, wherein the pump signal causes the switching circuitry to put the charge pump circuitry in a first charging mode associated with the first K-factor mode;
driving the charge pump circuitry of the IMD based on the charge signal, wherein the charge signal causes the switching circuitry to put the charge pump circuitry in a first pumping mode associated with the first K-factor mode;
putting the plurality of switches into a second switch configuration, wherein the second switch configuration is associated with a second K-factor mode selected from the group of K-factor modes; and
transferring, via the plurality of switches in the second switch configuration, energy from the battery to the hold capacitor.

17. The method of claim 16, further comprising:
determining that the IMD has entered a high current mode;
in response to determining that the IMD has entered the high current mode, determining a third K-factor mode from the group of K-factor modes based on a default voltage of the battery; and
putting the plurality of switches into a third switch configuration, wherein the third switch configuration is associated with a third K-factor mode selected from the group of K-factor modes.

18. The method of claim 17, wherein determining the third K-factor mode from the group of K-factor modes comprises selecting the third K-factor mode from a K-factor mode look up table.

* * * * *